United States Patent
Baumgarten et al.

(10) Patent No.: US 11,174,522 B2
(45) Date of Patent: Nov. 16, 2021

(54) METHODS AND COMPOSITIONS FOR IMPUTING OR PREDICTING GENOTYPE OR PHENOTYPE

(71) Applicant: PIONEER HI-BRED INTERNATIONAL, INC., Johnston, IA (US)

(72) Inventors: Andrew Baumgarten, Johnston, IA (US); Justin P Gerke, Urbandale, IA (US); Eli Rodgers-Melnick, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/813,942

(22) Filed: Mar. 10, 2020

(65) Prior Publication Data

US 2020/0291489 A1  Sep. 17, 2020

Related U.S. Application Data

(60) Provisional application No. 62/816,719, filed on Mar. 11, 2019, provisional application No. 62/833,497, filed on Apr. 12, 2019, provisional application No. 62/960,363, filed on Jan. 13, 2020.

(51) Int. Cl.
*C12Q 1/6895* (2018.01)
*G16B 20/00* (2019.01)

(52) U.S. Cl.
CPC .......... *C12Q 1/6895* (2013.01); *G16B 20/00* (2019.02); *C12Q 2600/13* (2013.01); *C12Q 2600/154* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

2018/0365372 A1  12/2018  Araya et al.

OTHER PUBLICATIONS

Way et al. Extracting a biologically relevant latent space from cancer transcriptomes with variational encoders Pacific Symposium on Biocomputing 2018 pp. 80-91 (Year: 2018).*
Hadjeres et al. GLSR-VAE: Geodesic Latent Space Regularization for Variational AutoEncoder Architectures IEEE Symposium Series on Computational Intelligence pp. 1-7 (Year: 2017).*
Chan, et al.; "A Likelihood-Free Inference Framework for Population Genetic Data using Exchangeable Neural Networks." 32nd Conference on Neural Information Processing Systems (NIPS 2018), Montréal, Canada.
Flangel, et al.; "The Unreasonable Effectiveness of Convolutional Neural Networks in Population Genetic Inference". Mol. Biol. Evol. (Dec. 4, 2018) 36(2):220-238.
Tucker, et al.; "Evaluating maize phenotypic variance, heritability, and yield relationships at multiple biological scales across agronomically relevant environments"; Plant, Cell, & Environment. (2019); 43(4):880-902.
"Variational Autoencoders."; Web page https://www.jeremyjordan.me/variational-autoencoders/, 23 pages, retrieved from Internet Archive Wayback Machine https://web.archive.org/web/*/https://www.jeremyjordan.me/variational-autoencoders/ Oct. 11, 2018).
Kingma, et al.; "Auto-encoding variational bayes"; In Proceedings of the International Conference on Learning Representations (ICLR) (2014).
Abdulaimma, Basma, et al.: "Extracting Epistatic Interactions in Type 2 Diabetes Genome-Wide Data Using Stacked Autoencoder," arXiv.org:1808.09517, Cornell University Library, Aug. 28, 2018 (Aug. 28, 2018), pp. 1-9.
Boyeau, Pierre, et al.: "Deep Generative Models for Detecting Differential Expression in Single Cells," Machine Learning in Computational Biology (MLCB), Oct. 4, 2019 (Oct. 4, 2019).
Clivio, Oscar, et al.: "Detecting Zero-Inflated Genes in Single-Cell Transcriptomics Data," Machine Learning in Computational Biology (MLCB), Oct. 10, 2019 (Oct. 10, 2019).
Cudic, Mihael, et al.: "Prediction of Sorghum Bi color Genotype from In-Situ Images Using Autoencoder-Identified SNPs," 2018 17th IEEE International Conference on Machine Learning and Applications, Dec. 17, 2018 (Dec. 2018), Issue 17, pp. 23-31.
Lopez, Romain, et al.: "Deep Generative Modeling for Single-cell Transcriptomics," Nature Methods, Dec. 2018 (Dec. 2018), vol. 15, No. 12, pp. 1053-1058.
Lopez, Romain, et al.: "A joint model of unpaired data from scRNA-seq and spatial transcriptomics for imputing missing gene expression measurements," ICML Workshop on Computational Biology, May 6, 2019 (May 6, 2019).
Xu, Chenling; et al.: "Harmonization and Annotation of Single-cell Transcriptomics data with Deep Generative Models," bioRxiv, Jan. 29, 2019 (Jan. 29, 2019).
ISR and Written Opinion of the International Searching Authority for international application No. PCT/US2020/021790, dated Aug. 18, 2020.

* cited by examiner

*Primary Examiner* — John S Brusca

(57) ABSTRACT

Methods and compositions to impute or predict genotype, haplotype, molecular phenotype, agronomic phenotypes, and/or coancestry are provided. Methods and compositions provided include using latent space to generate latent space representations or latent vectors that are independent of underlying genotypic or phenotypic data. The methods may include generating a universal latent space representation by encoding discrete or continuous variables derived from genotypic or phenotypic data into latent vectors through a machine learning-based encoder framework. Provided herein are universal methods of parametrically representing genotypic or phenotypic data obtained from one or more populations or sample sets to impute or predict a genotype or phenotype of interest.

25 Claims, 24 Drawing Sheets

| | | | | | | | | | |
|---|---|---|---|---|---|---|---|---|---|
| Markers | Marker | 1 | 2 | 3 | 4 | ... | M-3 | M-2 | M-1 | M |
| | Alleles | C/T | A/G | T/A | G/C | ... | A/T | I/D | A/C | I/D |
| | Encodings | 1/-1 | 1/-1 | 1/-1 | 1/-1 | ... | 1/-1 | 1/-1 | 1/-1 | 1/-1 |

| | | | | | | | | | |
|---|---|---|---|---|---|---|---|---|---|
| Example Genotype | Marker | 1 | 2 | 3 | 4 | ... | M-3 | M-2 | M-1 | M |
| | Alleles | C | G | T | Het | ... | Miss | D | A (0.9) C(0.1) | I |

| | | | | | | | | | | |
|---|---|---|---|---|---|---|---|---|---|---|
| Example Input | | 1 | -1 | 1 | 0 | ... | 0 | -1 | 0.8 | 1 | Channel 1: Obs. Homozygous |
| | | 0 | 0 | 0 | 1 | ... | -1 | 0 | 0 | 0 | Channel 2: Missing/Het |

M Markers over entire genome

*FIG. 13*

METHODS AND COMPOSITIONS FOR IMPUTING OR PREDICTING GENOTYPE OR PHENOTYPE

CROSS REFERENCE TO RELATED APPLICATIONS

This application claims the benefit of and priority to U.S. Provisional Application No. 62/960,363, filed Jan. 13, 2020, U.S. Provisional Application No. 62/833,497, filed Apr. 12, 2019, and U.S. Provisional Application No. 62/816,719, filed Mar. 11, 2019, each of which is incorporated herein by reference in entirety.

FIELD

This disclosure relates generally to the fields of imputation and prediction.

BACKGROUND OF THE INVENTION

Over the last 60 to 70 years, the contribution of plant breeding to agricultural productivity has been spectacular (Smith (1998) 53rd Annual corn and sorghum research conference, American Seed Trade Association, Washington, D.C.; Duvick (1992) Maydica 37: 69). This has happened in large part because plant breeders have been adept at assimilating and integrating information from extensive evaluations of segregating progeny derived from multiple crosses of elite, inbred lines. Conducting such breeding programs requires extensive resources. A commercial maize breeder, for example, may evaluate 1,000 to 10,000 F3 topcrossed progeny derived from 100 to 200 crosses in replicated field trials across wide geographic regions.

SUMMARY

In one embodiment, a universal method of parametrically representing genotypic or phenotypic association data from a training data set obtained from a population or a sample set to impute or predict a genotype and/or a phenotype in a test data obtained from a test population or a test sample data is provided herein. In some aspects, the method includes generating a universal continuous global latent space representation by encoding discrete or continuous variables derived from genome-wide genotypic or phenome-wide phenotypic association training data into latent vectors through a machine learning-based global encoder framework. In some examples, the encoder is an autoencoder. In some examples, the autoencoder is a variational autoencoder. In some aspects, the machine-learning based encoder framework is a generative adversarial network (GAN). In some aspects, the machine-learning based encoder framework is a neural network.

In some aspects, the global latent space or global latent space representation is independent of the underlying genotypic or phenotypic association used to represent the genetic or phenotypic information. For example, the generated latent representations are invariant to the selection of particular genotypic or phenotypic association features. In some aspects, the method includes generating a local latent representation by encoding a subset of the discrete or continuous variables derived from the genotypic or phenotypic association training data set into latent vectors through a machine learning-based local encoder framework, where the local latent space or local latent space representation is generated with inputs from the local encoder and the global encoder. In some examples, the local encoder is an autoencoder. In some examples, the autoencoder is a variational autoencoder. In some aspects, the machine-learning based encoder framework is a generative adversarial network (GAN). In some aspects, the machine-learning based encoder framework is a neural network.

In some aspects, the method includes decoding the global latent representation and the local latent representation by a local decoder, thereby imputing or predicting the genotype or phenotype of the test data by the combination of the decoded global latent representation and the local latent representation.

In some aspects, the genotypic association data includes a collection of genotypic markers or single nucleotide polymorphisms (SNPs) from a plurality of a genetically divergent population. The subset of the discrete variables may be a plurality of SNPs localized to a segment of the chromosome. In some aspects, the encoder is based on a neural network algorithm. In some aspects, the imputed or predicted phenotype is predicted yield gain. In some aspects, the imputed or predicted phenotype is root lodging, stalk lodging, brittle snap, ear height, grain moisture, plant height, disease resistance, drought tolerance, or a combination thereof. In some aspects, the imputed or predicted genotype is a plurality of haplotypes. In some aspects, the local decoder imputes or predicts local high-density (HD) SNPs.

In some aspects, the genotypic association data is obtained from populations of plants derived from two or more breeding programs, where the breeding programs do not comprise an identical set of markers or SNPs corresponding to the genotypic association data. In some aspects, the local decoder imputes local HD SNPs of one population based on the decoding of genotypic association data of another population. In some aspects, the local decoder imputes haplotypes for one population based on the decoding of genotypic association data of another population. In some aspects, the local decoder imputes or predicts a molecular phenotype including but not limited to gene expression, chromatin accessibility, DNA methylation, histone modifications, recombination hotspots, genomic landing locations for transgenes, transcription factor binding status, or a combination thereof. In some aspects, the local decoder imputes or predicts population coancestry for one or more of the test populations.

Also provided herein in an embodiment is a universal method of parametrically representing genotypic or phenotypic association data from a training data set obtained from a population or a sample set to infer a characteristic of interest, e.g. a desirable characteristic, in test data obtained from a test population or a test sample data. In some aspects, the method includes generating a universal continuous global latent space representation by encoding discrete or continuous variables derived from genome-wide genotypic or phenome-wide phenotypic association training data into latent vectors through a machine learning-based global encoder framework, where the global latent space or global latent space representation is independent of the underlying genotypic or phenotypic association. In some examples, the global encoder is an autoencoder. In some examples, the autoencoder is a variational autoencoder. In some aspects, the machine-learning based encoder framework is a generative adversarial network (GAN). In some aspects, the machine-learning based encoder framework is a neural network. In some aspects, the method includes decoding the global latent representation by a global decoder, thereby inferring the desirable characteristic of the test data by the decoded global latent representation.

In some aspects, the characteristic of interest, e.g. a desirable characteristic, is without limitation coancestry determination of two or more populations of plants or predicting yield gain or an agronomic phenotype of interest. In some aspects, the encoder is based on a neural network algorithm.

Also provided herein is a universal method of developing universal representation of genotypic or phenotypic data that includes receiving by a first neural network one or more training genotypic or phenotypic data, where the first neural network includes a global encoder. In some aspects, the method includes encoding by the global encoder, the information from one or more training genotypic or phenotypic data into latent vectors through a machine-learning based neural network training framework. In some aspects, the method includes providing the encoded latent vectors (generated from other genotypic or phenotypic data) to a second machine-learning based neural network, where the second neural network includes a decoder. In some aspects, the method includes training the decoder to predict a genotype or phenotype of interest for the encoded latent vectors based on a pre-specified or learned objective function. In some aspects, the method includes decoding by the decoder the encoded latent vector for the objective function. In some aspects, the method includes providing an output for the objective function of the decoded latent vector.

Also provided herein is a method of selecting an attribute of interest based on genotypic or phenotypic data. In some aspects, the method includes receiving by a first neural network one or more training global genotypic or phenotypic data, where the first neural network includes a global encoder. In some examples, the global encoder is an autoencoder. In some examples, the autoencoder is a variational autoencoder. In some aspects, the machine-learning based neural network is a generative adversarial network (GAN).

In some aspects, the method includes encoding by the global encoder, genotypic or phenotypic information from one or more training genotypic or phenotypic data into latent vectors. In some aspects, the method includes training the global encoder using the latent vectors to learn underlying genotypic or phenotypic correlations and/or relatedness. In some aspects, the method includes receiving by a second neural network one or more training local genotypic or phenotypic data, where the local genotypic or phenotypic data is directed to a subset of global genotypic or phenotypic data that corresponds to a certain attribute of interest, where the second neural network includes a local encoder. In some examples, the local encoder is an autoencoder. In some examples, the autoencoder is a variational autoencoder. In some aspects, the method includes encoding by the local encoder, the genotypic or phenotypic information from the one or more training local genotypic or phenotypic data into latent vectors. In some aspects, the method includes training the local encoder using the latent vectors to learn underlying genotypic correlations and/or relatedness for the attribute of interest. In some aspects, the method includes providing the encoded latent vectors from the global encoder and/local encoder to a third neural network, where the third neural network includes a decoder. In some aspects, the method includes training the decoder to predict the attribute of interest for the encoded latent vectors from the global encoder and/the local encoder using a pre-specified or learned objective function. In some aspects, the method includes decoding by the decoder, the encoded latent vectors for the objective function. In some aspects, the method includes providing an output for the objective function of the decoded latent vector.

The decoder may include one or more decoders. In some aspects, the decoder is a local decoder. In some aspects, the decoder is a global decoder and decodes the encoded latent vectors from the global encoder. In some aspects, the global training genotypic data includes markers across the genome. In some aspects, the local genotypic data is from a specific chromosomal genomic region of interest or allele. In some aspects, the method includes training the global encoder and decoder simultaneously.

In some aspects, the local attribute may include without limitation SNPs, alleles, markers, quantitative trait loci (QTLs), gene expression, phenotypic variation, metabolite level, or combinations thereof. In some aspects, the encoder may be an autoencoder. In some aspects, the autoencoder is a variational autoencoder.

In some aspects, the training genotypic data includes without limitation SNPs or indels (INsertions/DELetions) sequence information. In some aspects, the training genotypic or phenotypic data includes sequence information from in silico crosses. In some aspects, the encoder weights are updated relative to a reconstruction error so that the training genotypic or phenotypic data information is separated within the latent space. In some aspects, the decoder is trained on existing genotypic or phenotypic data.

Also provided herein is a computer system for generating genotypic or phenotypic data determinations. In one embodiment, the system includes a first neutral network that includes an encoder configured to encode genotypic or phenotypic information from one or more training genotypic or phenotypic data into universal latent vectors, where the encoder has been trained to represent genotypic or phenotypic associations through a machine-learning based neural network framework and a second neural network includes decoder configured to decode the encoded latent vectors and generate an output for an objective function. In some aspects, the encoder may be an autoencoder. In some aspects, the autoencoder is a variational autoencoder.

Also provided herein in an embodiment is a universal method of parametrically representing genotypic or phenotypic data obtained from a population or a sample set to impute or predict a desired genotype and/or phenotype. In some aspects, the method includes generating a universal latent space representation by encoding discrete or continuous variables derived from genotypic or phenotypic data into latent vectors through a machine learning-based encoder framework, where the latent space or latent space representation is independent of the underlying genotypic or phenotypic data. In some aspects, the method includes decoding the latent representation by a decoder, thereby imputing or predicting the desired genotype or phenotype by the decoded latent representation.

In some aspects, the genotypic data is a collection of genotypic markers or single nucleotide polymorphisms (SNPs) from a plurality of genetically divergent populations. In some aspects, a subset of the discrete variables is a plurality of SNPs localized to a segment of a chromosome. In some aspects, the encoder is based on a neural network algorithm. In some aspects, the imputed or predicted phenotype is yield gain, root lodging, stalk lodging, brittle snap, ear height, grain moisture, plant height, disease resistance, drought tolerance, or a combination thereof.

In some aspects, the imputed or predicted genotype is a plurality of haplotypes.

In some aspects, the decoder imputes or predicts SNPs, such as local high-density (HD) SNPs, and/or indels.

In some aspects, genotypic data is obtained from populations of plants derived from two or more breeding programs, where the breeding programs do not have an identical set of markers or SNPs corresponding to the genotypic data. In some aspects, the decoder imputes or predicts local HD SNPs of one population based on the decoding of genotypic data of another population. In some aspects, the decoder imputes or predicts haplotypes for one population based on the decoding of genotypic data of another population.

In some aspects, the decoder imputes or predicts a molecular phenotype selected from gene expression, chromatin accessibility, DNA methylation, histone modifications, recombination hotspots, genomic landing locations for transgenes, transcription factor binding status, or a combination thereof. In some aspects, the decoder imputes or predicts population coancestry for one or more of the populations.

Also provided herein is a computer system for generating genotypic or phenotypic data determinations. In one embodiment, the system includes a first network that includes an encoder configured to encode genotypic or phenotypic information from one or more training genotypic or phenotypic data into universal latent vectors, where the encoder has been trained to represent genotypic or phenotypic associations through a machine-learning based network framework and a second network includes a decoder configured to decode the encoded latent vectors and generate an output for an objective function. In some aspects, the encoder may be an autoencoder. In some aspects, the autoencoder is a variational autoencoder. In some aspects, the machine-learning based neural network framework is a generative adversarial network (GAN). In some aspects, the machine-learning based neural framework is a neural network.

Also provided herein is a computing device for training a neural network for translation between genotyping platforms. In one embodiment, the computing device includes a memory and one or more processors. The one or more processors configured to obtain training data associated with at least two populations from the genotyping platforms; generate a first latent space representation by encoding variables derived from the training data into a first set of latent vectors using a first encoder machine learning network; generate a second latent representation by encoding a subset of the variables from the training data into a second set of latent vectors using a second encoder machine learning network; combine the global latent representation and the local latent representation to train a decoder machine learning network; and decode one or more latent vectors from the combined global and local latent representations to impute or predict a genotype or a phenotype of the training data corresponding to the one or more latent vectors using the decoder machine learning network.

In some embodiments, the training data may include genome-wide genotypic association training data and/or phenome-wide phenotypic association training data.

In some embodiments, the genome-wide genotypic association training data may include genotypic markers, indels, and/or single nucleotide polymorphisms (SNPs) from a plurality of genetically divergent populations.

In some embodiments, the subset of the variables may be a plurality of indels and/or single nucleotide polymorphisms (SNPs) localized to a segment of a chromosome.

In some embodiments, the genome-wide genotypic association training data may be obtained from populations of plants derived from two or more breeding programs. The breeding programs may not include an identical set of markers, indels, and/or single nucleotide polymorphisms (SNPs) corresponding to the genotypic association data.

In some embodiments, the first encoder machine learning network may include a global variational autoencoder framework.

In some embodiments, the second encoder machine learning network may include a local variational autoencoder framework.

In some embodiments, the first latent space representation may be independent of the underlying genotypic or phenotypic association.

In some embodiments, the imputed or predicted phenotype may be predicted yield gain.

In some embodiments, the imputed or predicted phenotype may be root lodging, stalk lodging, brittle snap, ear height, grain moisture, plant height, disease resistance, and/or drought tolerance.

In some embodiments, the imputed or predicted genotype may be a plurality of haplotypes.

In some embodiments, the imputed or predicted genotype may be local high-density (HD) SNPs.

In some embodiments, to decode the one or more latent vectors from the combined global and local latent representations may include to decode the one or more latent vectors from the combined global and local latent representations to impute or predict local high-density (HD) SNPs of a first population based on the decoding of genome-wide genotypic association training data of a second population.

In some embodiments, to decode the one or more latent vectors from the combined global and local latent representations may include to decode the one or more latent vectors from the combined global and local latent representations to impute or predict haplotypes for a first population based on the decoding of genotypic association data of a second population.

In some embodiments, the imputed or predicted phenotype may include gene expression, chromatin accessibility, DNA methylation, histone modifications, recombination hotspot, genomic landing locations for transgenes, and/or transcription factor binding status.

In some embodiments, to decode the one or more latent vectors from the combined global and local latent representations may include to decode the one or more latent vectors from the combined global and local latent representations to impute or predict population coancestry for one or more of the test populations of the training data.

Also provided herein is a system for training a neural network for translation between genotyping platforms is provided. The system includes one or more servers and a computing device communicatively coupled to the one or more servers. Each of the one or more server storing training data associated with one or more populations. The computing device further includes a memory and one or more processors. The one or more processors are configured to obtain training data; generate a first latent space representation by encoding variables derived from the training data into a first set of latent vectors using a first encoder machine learning network; generate a second latent representation by encoding a subset of the variables from the training data into a second set of latent vectors using a second encoder machine learning network; combine the global latent representation and the local latent representation to train a decoder machine learning network; and decode one or more latent vectors from the combined global and local latent representations to impute or predict a genotype or a phenotype of the training data corresponding to the one or more latent vectors using the decoder machine learning network.

BRIEF DESCRIPTION OF THE DRAWINGS

The invention can be more fully understood from the following detailed description and the accompanying drawings which form a part of this application.

FIG. 9A shows a reduced-dimensionality visualization of the global latent space of two populations (i.e., Population 1 and Population 2) with disjoint marker sets. Despite disjointed inputs, the latent representations of a germplasm originated from Population 2 genotyped on the Population 1 marker platform leads to clustering with Population 1's genotyped versions of those inbred lines.

FIG. 12A illustrates the accuracy and power of the haplotype-pooling approach.

FIG. 12B and FIG. 12C illustrate examples of detected peaks using haplotype pooling. Grey lines correspond to tissue peaks that were only detected using haplotype pooling. FIG. 12B illustrates the detection of peaks at alternative TSSs of a single gene, while FIG. 12C illustrates the detection of peaks at a known major QTL in maize that is 65 kb from the nearest protein-coding gene.

FIGS. 13-20 are example inputs and outputs of encoders and decoders.

DETAILED DESCRIPTION

It is to be understood that this invention is not limited to particular embodiments, which can, of course, vary. It is also to be understood that the terminology used herein is for the purpose of describing particular embodiments only, and is not intended to be limiting. Further, all publications referred to herein are each incorporated by reference for the purpose cited to the same extent as if each was specifically and individually indicated to be incorporated by reference herein.

Methods and systems provided herein minimize the labor intensive steps normally associated with machine learning application such as for example, the construction of a feature set that is relevant for the scope of the problem, satisfaction of the constraints of the algorithm(s) to be used, and minimal prediction error on testing data.

Figure 1:
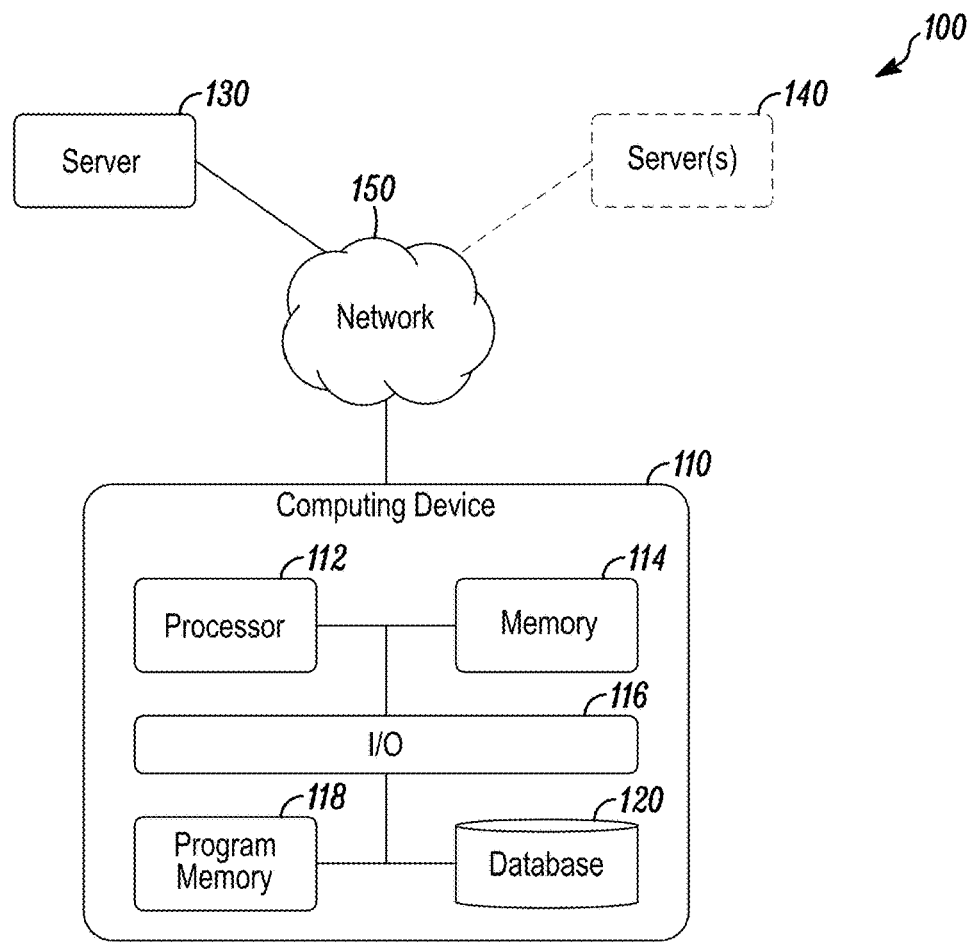
FIG. 1 is a block diagram illustrating an exemplary computer system including a server and a computing device according to an embodiment as disclosed herein.

Referring to FIG. 1, a block diagram of a computer system 100 for parametrically representing genotypic or phenotypic association data is shown. To do so, the system 100 may include a computing device 110 and a server 130 that is associated with a computer system. The system 100 may further include one or more servers 140 that are associated with other computer systems such that the computing device 110 may communicate with different computer systems running different platforms. However, it should be appreciated that, in some embodiments, a single server (e.g., a server 130) may run multiple platforms. The computing device 110 is communicatively coupled to the one or more servers 130, 140 via a network 150 (e.g., a local area network (LAN), a wide area network (WAN), a personal area network (PAN), the Internet, etc.).

In use, the computing device 110 may predict genotype and/or phenotype associations by training a neural network for universal translation between genotyping platforms. More specifically, the computing device 110 may obtain data from multiple or potentially disjoint platforms and translate the data into a universal, platform independent (e.g., marker-independent), latent space. For example, in the context of genomic characterization, a smooth spatial organization of the latent space captures varying levels of ancestral relationships that are present within a dataset. Genomic variation within a population, such as a plant breeding program, may be characterized by a variety of methods. For example, genotypes are characterized with a common platform that interrogates localized variants such as single nucleotide polymorphisms (SNPs) and/or insertions/deletions (indels). Due to the ancestral recombination and demographic history of the population, these variants tend to co-segregate within linked segments (haplotypes). Further, single genotypes may then be further characterized by the set of haplotypes they contain. As described further below, variational autoencoders (VAEs) may be used to compress the information contained within a given set of production markers to a common, marker-invariant, latent space capable of capturing these co-segregation patterns genome-wide.

In general, the computing device 110 may include any existing or future devices capable of training a neural network. For example, the computing device may be, but not limited to, a computer, a notebook, a laptop, a mobile device, a smartphone, a tablet, wearable, smart glasses, or any other suitable computing device that is capable of communicating with the server 130.

The computing device 110 includes a processor 112, a memory 114, an input/output (I/O) controller 116 (e.g., a network transceiver), a memory unit 118, and a database 120, all of which may be interconnected via one or more address/data bus. It should be appreciated that although only one processor 112 is shown, the computing device 110 may include multiple processors. Although the I/O controller 116 is shown as a single block, it should be appreciated that the I/O controller 116 may include a number of different types of I/O components (e.g., a display, a user interface (e.g., a display screen, a touchscreen, a keyboard), a speaker, and a microphone).

The processor 112 as disclosed herein may be any electronic device that is capable of processing data, for example a central processing unit (CPU), a graphics processing unit (GPU), a system on a chip (SoC), or any other suitable type of processor. It should be appreciated that the various operations of example methods described herein (i.e., performed by the computing device 110) may be performed by one or more processors 112. The memory 114 may be a random-access memory (RAM), read-only memory (ROM), a flash memory, or any other suitable type of memory that enables storage of data such as instruction codes that the processor 112 needs to access in order to implement any method as disclosed herein. It should be appreciated that, in some embodiments, the computing device 110 may be a computing device or a plurality of computing devices with distributed processing.

As used herein, the term "database" may refer to a single database or other structured data storage, or to a collection of two or more different databases or structured data storage components. In the illustrative embodiment, the database 120 is part of the computing device 110. In some embodiments, the computing device 110 may access the database 120 via a network such as network 150. The database 120 may store data (e.g., input, output, intermediary data) that is necessary to generate a universal continuous latent space representation. For example, the data may include genotypic data, such as single nucleotide polymorphisms (SNPs), genetic markers, haplotype, sequence information, and/or phenotype data that are obtained from one or more servers 130, 140.

The computing device 110 may further include a number of software applications stored in a memory unit 118, which may be called a program memory. The various software applications on the computing device 110 may include specific programs, routines, or scripts for performing processing functions associated with the methods described herein. Additionally or alternatively, the various software applications on the computing device 110 may include general-purpose software applications for data processing, database management, data analysis, network communication, web server operation, or other functions described herein or typically performed by a server. The various software applications may be executed on the same computer processor or on different computer processors. Additionally, or alternatively, the software applications may interact with various hardware modules that may be installed within or connected to the computing device 110. Such modules may implement part of or all of the various exemplary method functions discussed herein or other related embodiments.

Although only one computing device 110 is shown in FIG. 1, the server 130, 140 is capable of communicating with multiple computing devices similar to the computing device 110. Although not shown in FIG. 1, similar to the computing device 110, the server 130, 140 also includes a processor (e.g., a microprocessor, a microcontroller), a memory, and an input/output (I/O) controller (e.g., a network transceiver). The server 130, 140 may be a single server or a plurality of servers with distributed processing. The server 130, 140 may receive data from and/or transmit data to the computing device 110.

The network 150 is any suitable type of computer network that functionally couples at least one computing device 110 with the server 130, 140. The network 150 may include a proprietary network, a secure public internet, a virtual private network and/or one or more other types of networks, such as dedicated access lines, plain ordinary telephone lines, satellite links, cellular data networks, or combinations thereof. In embodiments where the network 150 comprises the Internet, data communications may take place over the network 150 via an Internet communication protocol.

Figure 2:
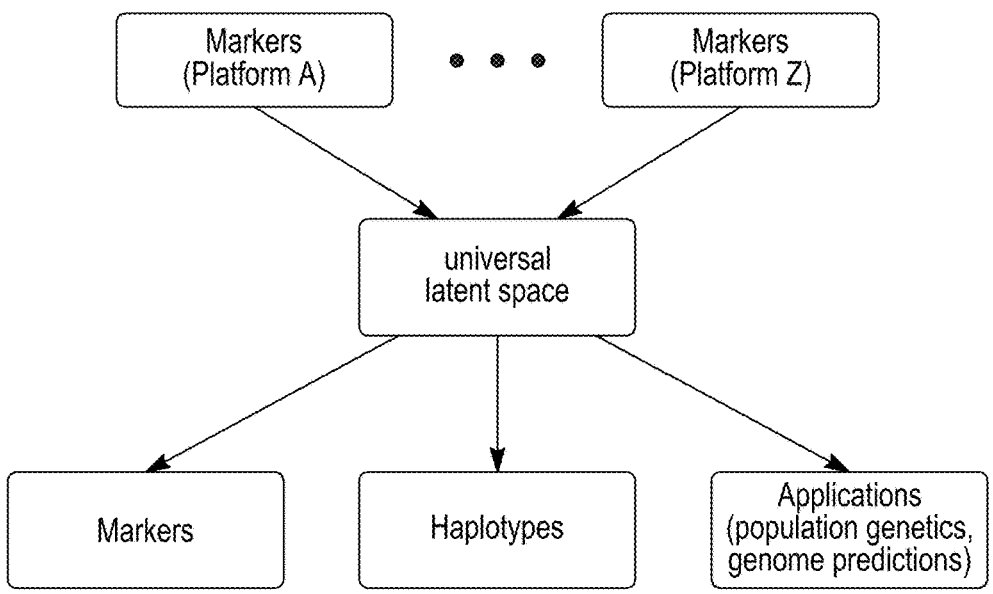
FIG. 2 is a schematic that illustrates the use of marker information from two different platforms to impute markers, haplotypes, or other information, e.g. population genetics, genomic prediction, based on latent representations of the underlying marker information.

Referring now to FIG. 2, a schematic diagram illustrating a use of marker information from multiple platforms to construct a universal latent representation of genotypes that are insensitive to an input marker platform is shown. As described further below, the universal latent representations may be used for various downstream analyses such as marker imputation, haplotype imputation, genomic prediction, or population genetic inference. To do so, various genotype/phenotype applications may involve using variational autoencoders (VAE). One such example is for universal translation between genotyping platforms. The VAE are hybrids of deep neural networks and probabilistic graphical models that enable construction of a compressed latent representation that is independent of the underlying data generation (e.g., genotyping platform) and serves as a basis of imputing characteristics of a desired data set (e.g., multiple germplasm characterization). Because time spent on custom tailoring for machine-learning applications often produces an application of limited scope, the use of deep learning approaches reduces the labor and broaden the application of machine learning by automating the construction of optimal feature spaces based on raw inputs, which were utilized to build a variety of VAEs described herein.

The core of VAE is rooted in Bayesian inference, which includes modeling of the underlying probability distribution of data, such that new data can be sampled from that distribution, which is independent of the dataset that resulted in the probability distribution. VAEs have a property that separates them from standard autoencoders that is suitable for generative modeling: the latent spaces that VAEs generate are, by nature of the framework, probability distributions, thereby allowing simpler random sampling and interpolation for desirable end-uses. VAEs accomplish this latent space representation by making its encoder not output an encoding vector of size n, rather, outputting two vectors of size n: a vector of means, $\mu$, and another vector of standard deviations, $\sigma$. Some of the basic notions for VAE include for example:

X: data that needs to be modeled, for example, genotypic data (such as SNPs, markers, haplotype, sequence information)

z: latent variable

P(X): probability distribution of the data, for example, genotypic data

P(z): probability distribution of latent variable (e.g., genotypic associations from the underlying genotypic data)

P(X|z): distribution of generating data given latent variable, e.g. prediction or imputation of the desired outcome based on the latent variable.

VAE is based on the principle that if there exists a hidden variable z, which generates an observation or an outcome x, then one of the objectives is to model the data, i.e., to find P(X). However, one can observe x, but the characteristics of z need to be inferred. Thus, p(z|x) needs to be computed.

$$p(z|x)=p(x|z)p(z)/p(x)$$

However, computing p(x) is based on probability theory, in relation to z. This function can be expressed as follows:

$$p(x)=\int p(x|z)p(z)dz$$

While the p(x) function is an intractable distribution, variational inference is used to optimize the joint distribution of x and z. The function p(z|x) is approximated by another distribution q(z|x), which is defined such that it is a tractable distribution. The parameters of q(z|x) are defined such that they are highly similar to p(z|x) and therefore, it can be used to perform approximate inference of the intractable distribution. KL divergence is a measure of difference between two probability distributions. Therefore, if the goal is to minimize the KL divergence between the two distributions, this minimization function is expressed as:

$$\min KL(q(z|x)\|p(z|x))$$

This expression is minimized by maximizing the following:

$$E q(z|x) \log p(x|z) - KL(q(z|x)\|p(z))$$

Reconstruction likelihood is represented by the first part, and the second term penalizes departure of probability mass in q from the prior distribution, p. q is used to infer hidden variables (latent representation) and this is built into a neural network architecture where the encoder model learns the mapping relation from x to z and the decoder model learns the mapping from z back to x. Therefore, the neural network for this function includes two terms—one that penalizes reconstruction error or maximizes the reconstruction likelihood and the other that encourages the learned distribution q(z|x) to be highly similar to the true prior distribution p(z), which is assumed to follow a unit Gaussian distribution, for each dimension j of the latent space. This is represented by:

$$\mathcal{L}(x, \hat{x}) + \sum_j KL(q_j(z|x)\|p(z))$$

It should be appreciated that the variational autoencoder is one of several techniques that may be used for producing compressed latent representations of raw samples, for example, genotypic association data. Like other autoencoders, the variational autoencoder places a reduced dimensionality bottleneck layer between an encoder and a decoder neural network. Optimizing the neural network weights relative to the reconstruction error then produces separation of the samples within the latent space. However, unlike generative adversarial networks (GAN), the encoder neural network's outputs are parameterized univariate Gaussian distributions with standard N(0,1) priors. Thus, unlike other autoencoders, which tend to memorize inputs and place them in arbitrarily small locations within the latent space, the variational autoencoder produces a smooth, continuous latent space in which semantically-similar samples tend to be geometrically close—e.g., haplotypes that co-segregate to provide a certain phenotype.

For example, in the context of genomic characterization, a smooth spatial organization of the latent space captures varying levels of ancestral relationships that are present within a dataset. Genomic variation within a population such as a plant breeding program may be characterized by a variety of methods. For example, genotypes are characterized with a common platform that interrogates localized variants such as single nucleotide polymorphisms (SNPs) and/or insertions/deletions (indels). Due to the ancestral recombination and demographic history of the population, these variants tend to co-segregate within linked segments (haplotypes). Further, single genotypes may then be further characterized by the set of haplotypes they contain. For example, as described further below, VAEs may be used to compress the information contained within a given set of production markers to a common, marker-invariant, latent space capable of capturing these co-segregation patterns genome-wide.

Figure 3:
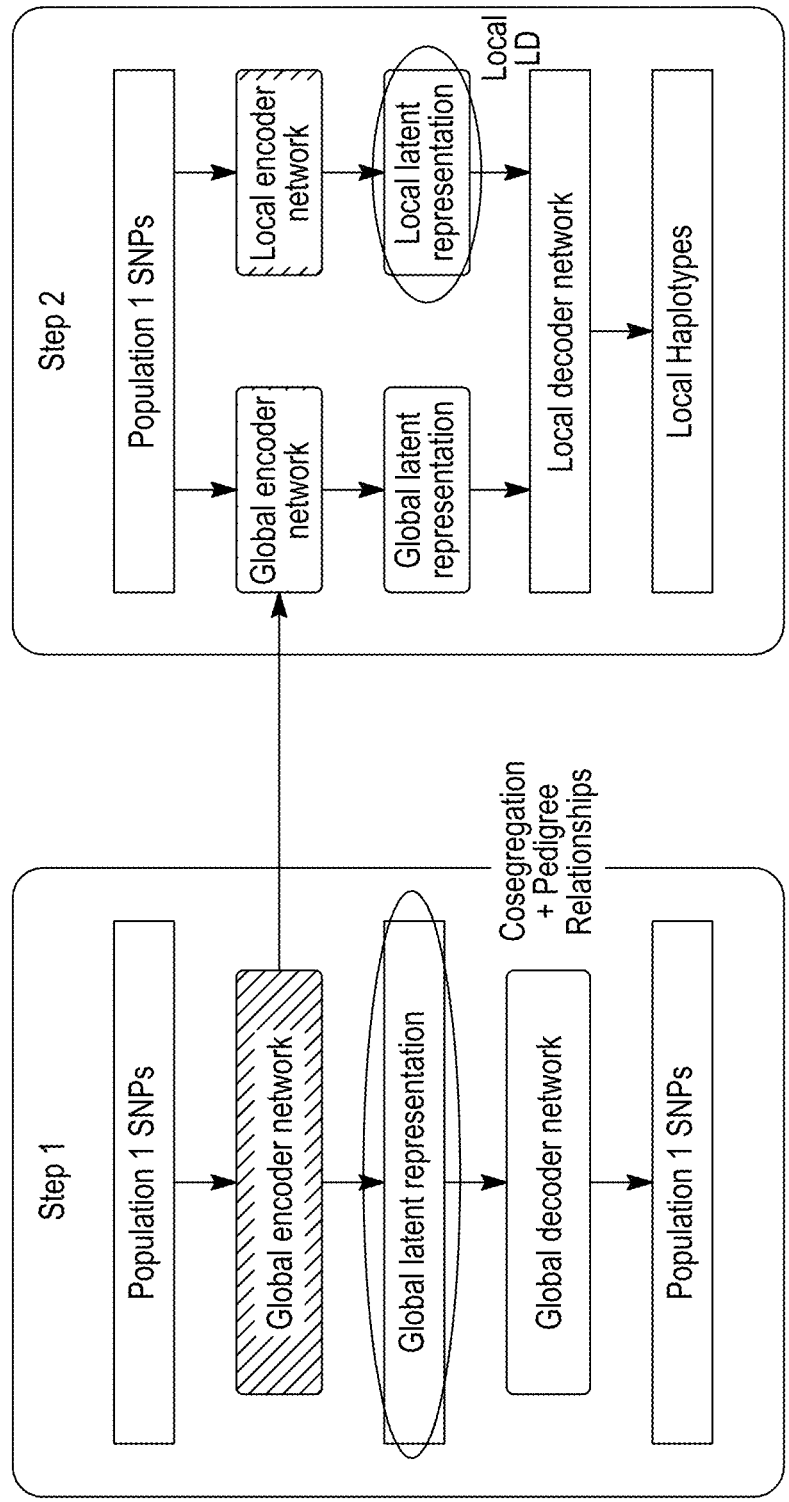
FIG. 3 is a schematic illustrating the steps in one embodiment of a method of imputing the haplotypes onto germplasm based on latent representations of the underlying SNP information.

In an embodiment that characterizes genotypic associations, certain features of VAE may be divided into two sources: first, large linked regions associated with recent family structure and second, highly localized statistical associations—linkage disequilibrium (LD)—associated with ancient ancestry. To do so, as illustrated in FIG. 3, the deep neural networks, including a global encoder network, a local encoder network, and a local decoder network, are structured around these features by training two stages.

First, a VAE may be trained with inputs from across a genome. The inputs may include production markers. The outputs that determine the reconstruction error may also be taken from across the genome; they may constitute a different set from the input markers. The resultant latent space from the global encoder geometrically is configured to approximate recent kinship and longer-distance ancestral relationships among the germplasm. For example, as illustrated in FIG. 3, a global encoder is trained to represent genetic marker co-segregation and pedigree relationships based on a full set of input SNPs, and this is encoded within the global latent representation.

Second, local encoder and decoder neural networks may then be trained for each smaller subsection of the genome. The local encoder network provides a high resolution representation of the LD within a local genomic region. One such input to a local encoder, for example, is a subset of the production SNPs localized to the encompass the region of interest (e.g. a chromosome or a particular QTL). Once the local encoder is trained, the local decoder network may be trained to impute haplotypes within a defined genomic bin of that local region. The input to the local decoder is the combination of latent outputs from the local encoder and the—now frozen—global encoder, as shown in FIG. 3. The reconstruction objective for the local encoder/decoder combination, for example, is a set of markers within a small contiguous region (e.g. 1 centimorgan (cM) on a genetic map), which encourages the local latent representation to capture the highly localized linkage disequilibrium (LD) that may have been overlooked by the global encoder. It should be appreciated that, in some embodiments, the contiguous region may be defined in physical coordinates. Once constructed, the combination of the global latent space and the local latent space within a region provide a compressed representation of available information necessary for haplotype reconstruction and—by extension—any inference method conditioned upon genotypic data.

Figure 4:
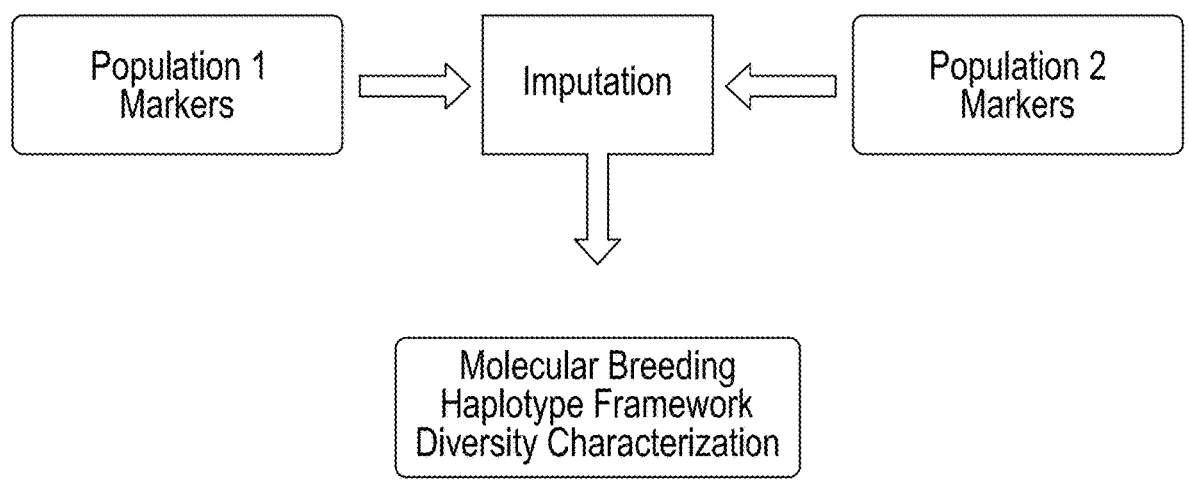
FIG. 4 is a flowchart showing one example of imputing separate marker populations onto germplasm, where the historical relationships of the germplasm are unknown, based on latent representations of the underlying marker information, and using the resulting imputed information to facilitate molecular breeding applications, haplotype framework generation, and/or diversity characterization that is independent of the genotyping platform.
Figure 5A:
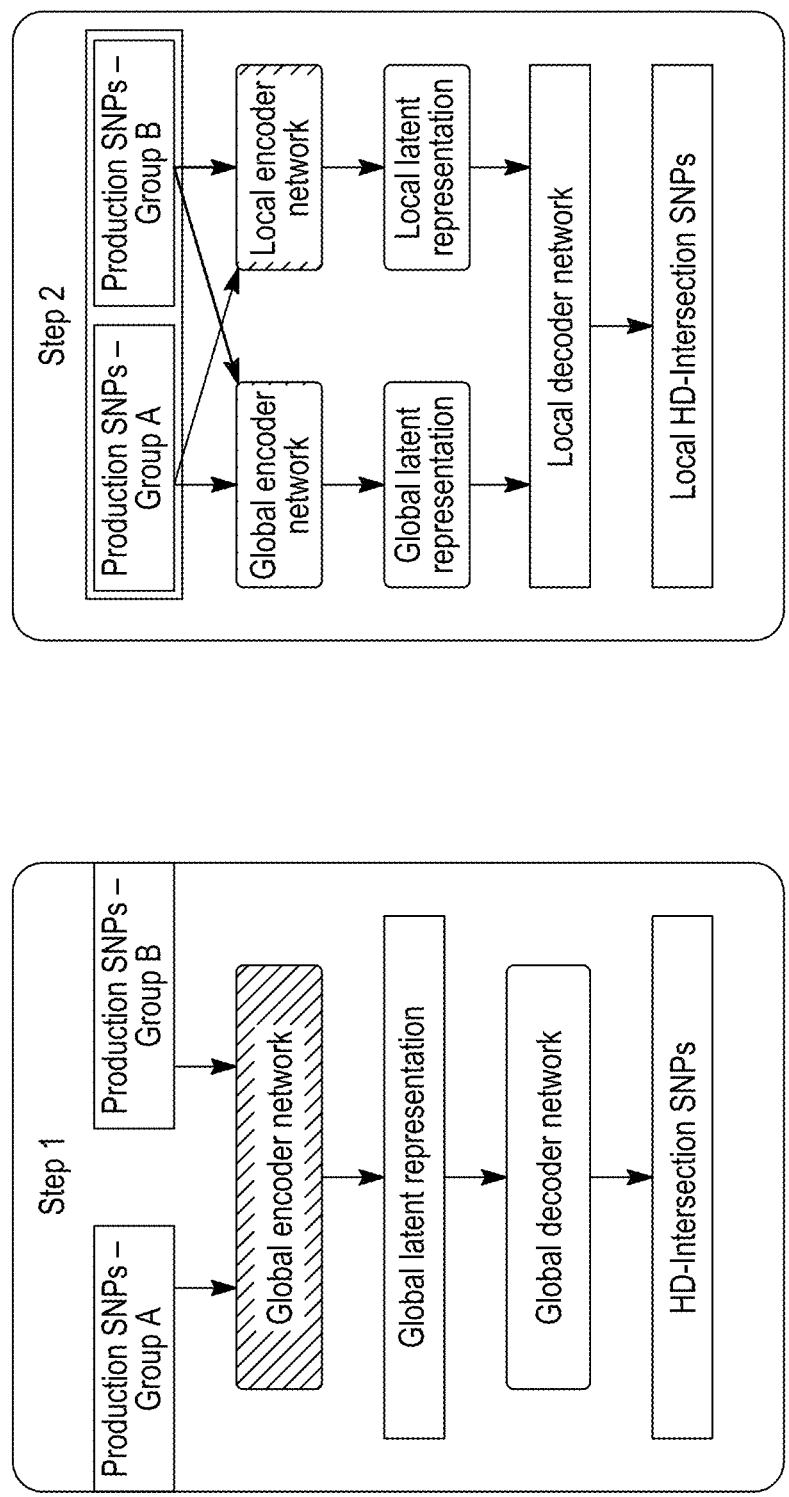
FIG. 5A and FIG. 5B is a schematic illustrating the steps in one embodiment of a method of imputing combined production markers from two different groups, Group A and Group B. Steps 1 and 2 are shown in FIG. 5A and Step 3 is shown in FIG. 5B.
Figure 5B:
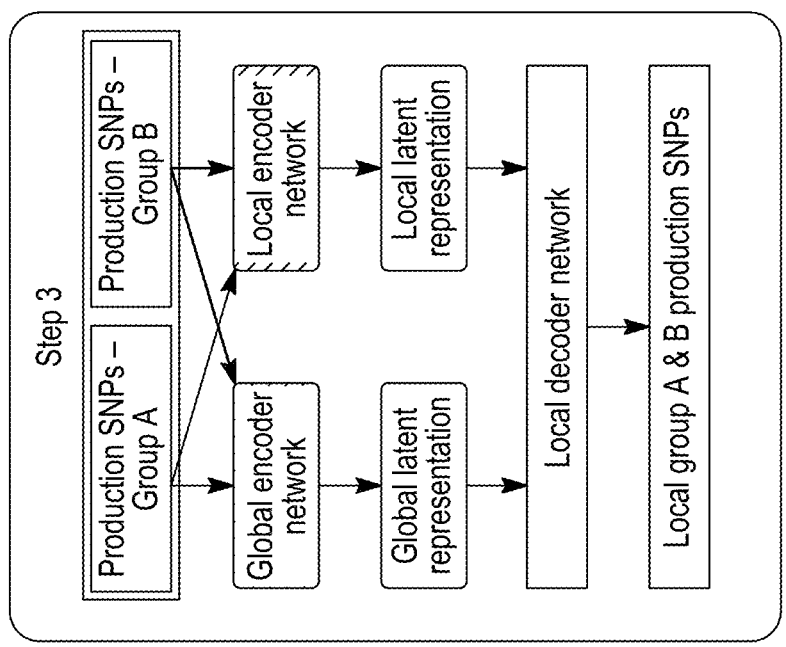

It should be appreciated that in some embodiments, for example, as shown in FIGS. 4 and 5, the encoder inputs to the global encoder and the local encoder may include production markers from multiple or potentially disjoint platforms for imputing a unified set of markers onto separate populations of germplasm. As shown in FIG. 4, two populations may have unknown historical populations and/or little or no shared markers between their legacy marker platforms. The imputation process described in FIGS. 5A and 5B, which is conditioned on the latent representations of the underlying marker information, produces a unified view of markers across the legacy platforms in both populations. This unified marker set then enables molecular breeding applications, haplotype framework generation, and/or diversity characterization that is independent of the original genotyping platform.

The imputation process shown in FIGS. 5A and 5B is similar to one described in FIG. 3. However, the imputation process of FIGS. 5A and 5B is different in that combined latent representations may be produced by inputting combined production markers from two different groups or populations of germplasm, Group A and Group B. Although two groups are shown in FIGS. 5A and 5B, it should be appreciated that production markers from more than two groups may be used as inputs to produce combined latent representations. Step 1 of FIG. 5A illustrates the construction of a global latent representation, which represents marker co-segregation and pedigree relationships independently of the group of origin due to the need to reconstruct a common set of high-density SNPs between the group. Step 2 of FIG. 5A illustrates the training of local encoder networks that provide a latent representation of the local LD within each region, after accounting for the global relationships. The combined latent representations then allow for imputation of a unified set of production SNPs through local decoder networks, illustrated in step 3 of FIG. 5B.

Figure 14:
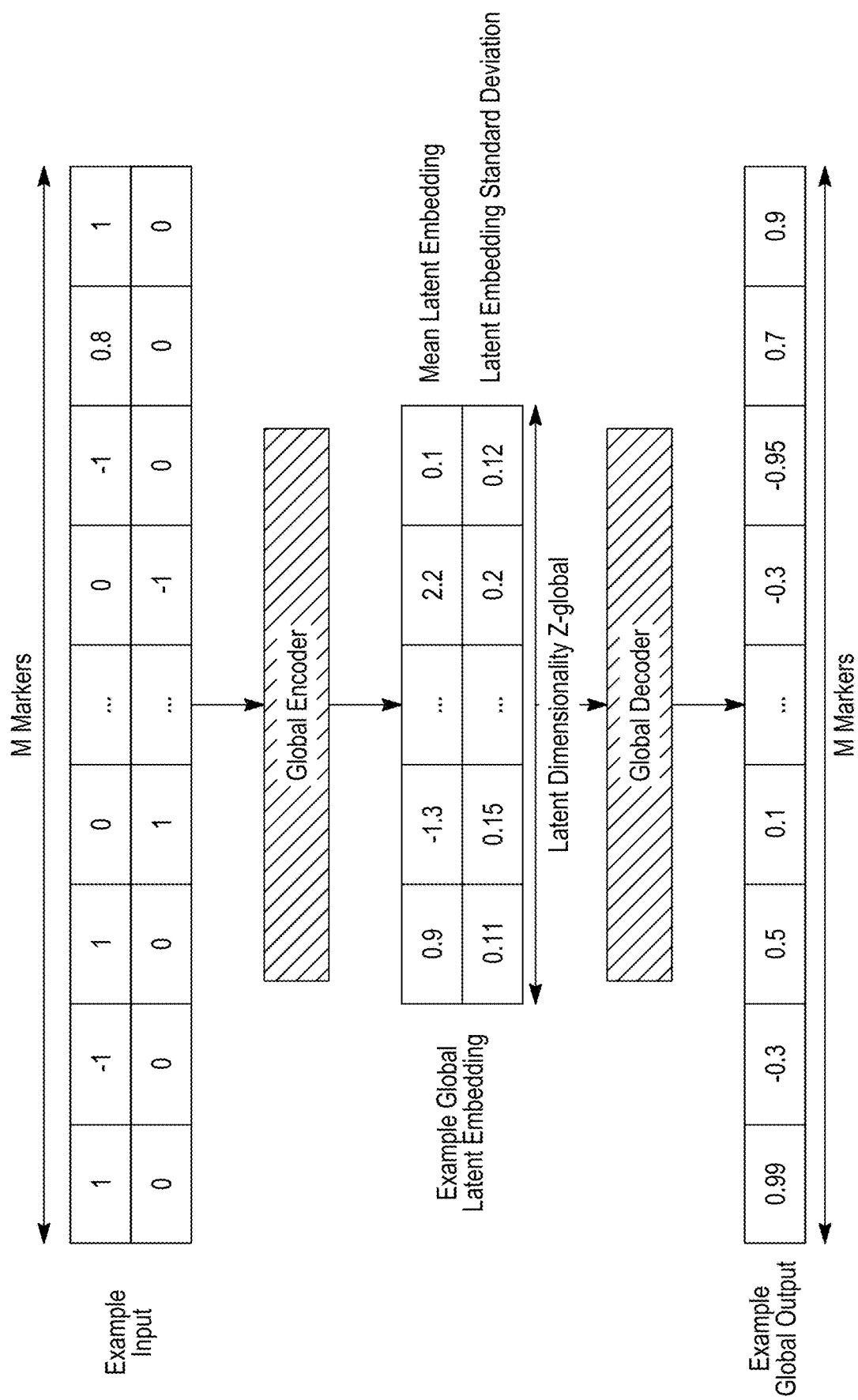
Figure 15:
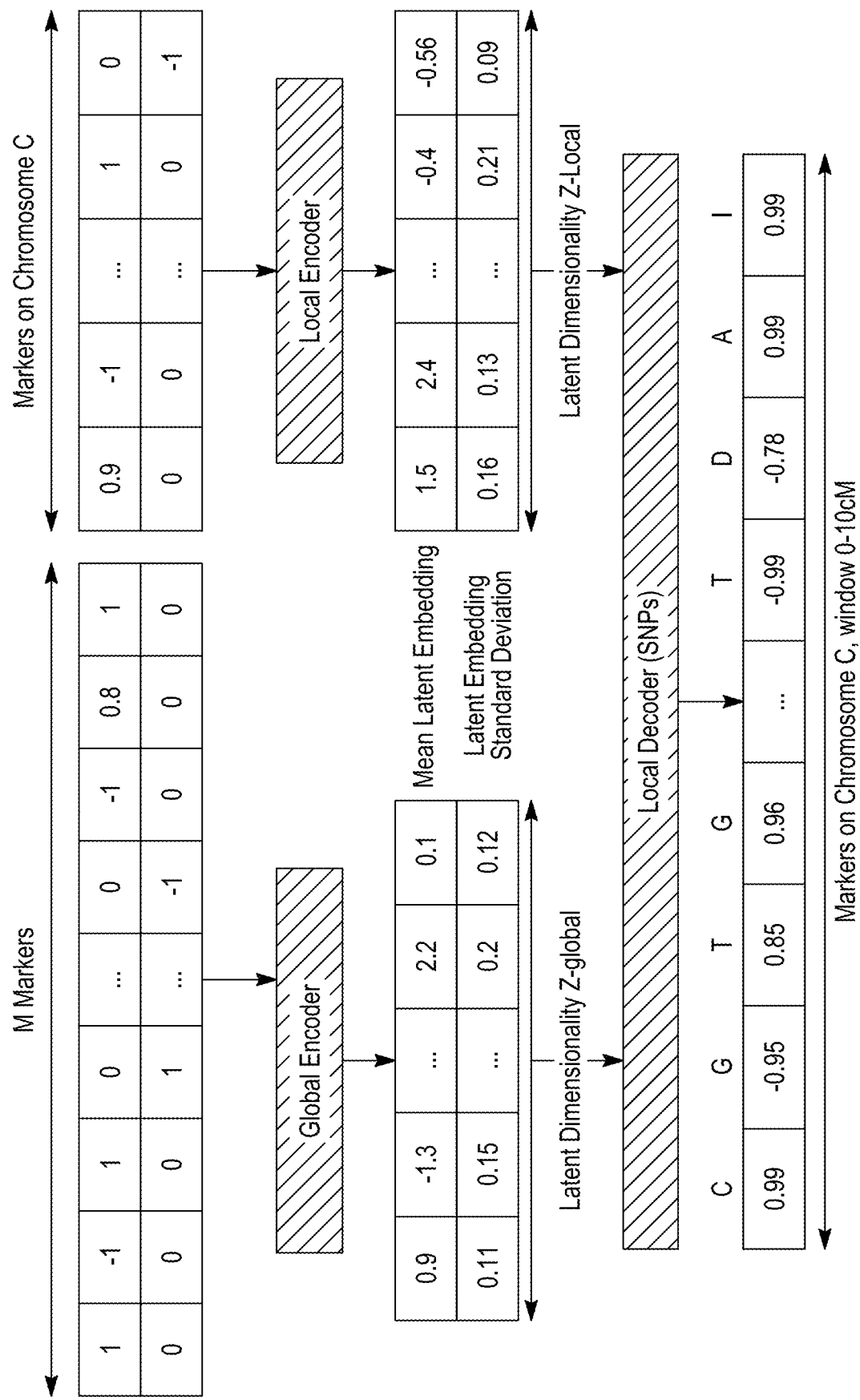

Referring now to FIGS. 13-15, examples of input to the global and local encoders and output from the local decoder are shown. In the illustrative embodiment, the global encoder is trained with input that is coded as homozygous, heterozygous, or missing for a particular allele. For example, as shown in FIG. 13, a numeric value(s) is assigned to each marker indicating whether the allele is homozygous, heterozygous, or missing. In the illustrative embodiment, there are M number of markers over entire genome, and each marker is a choice between bases (adenine (A), guanine (G), cytosine (C), and thymine (T)) or between insertions and deletions (I, D). Each marker has a choice between a first base and a second base at a specific allele. If an example genotype (i.e., a sample) has the homozygous first base, then that marker is assigned a numeric value 1. If, however, the example genotype has the homozygous second base, then that marker is assigned a numeric value −1. It should be appreciated that, in the illustrative embodiment, the markers are probabilistic calls rather than hard calls, as indicated by Marker M−1. For example, for Marker M−1, based on genotypes of the sample's parents, it may predict that the sample is likely to have the homozygous first base A with a probability of 0.9 and the homozygous second base C with a probability of 0.1. As such, in the illustrative embodiment, an example input for that marker is calculated by (0.9×1)+(0.1x−1)=0.8.

In the illustrative embodiment, Channel 2 is also generated to indicate whether the marker is homozygous (0), heterozygous (1), or missing (−1). However, it should be appreciated that, although two channels are shown in FIG. 13, only one channel may be used as input to one or more encoders. It should also be appreciated that any number, value, or code may be assigned in order to distinguish these features to generate formatted input to one or more encoders.

As shown in FIG. 14, the encoding of markers across the genome is then used to train the global encoder to produce a representation of a latent distribution. The global decoder then takes a sample from the latent distribution as an input and reconstructs the original marker set (M markers). For example, the value 0.99 in the first column of the Example Global Output indicates that there is a high probability of a presence of a first allele (i.e., homozygous base C in this example as indicated in FIG. 13) at the locus that corresponds to Marker 1. Whereas, the value −0.95 in the third to the last column of the Example Global Output indicates that there is a high probability of second allele (i.e., deletion of a base in this example as indicated in FIG. 13) at the locus that corresponds to Marker M−2. The value −0.3 in the second column indicates that it is uncertain probability of second allele (i.e., homozygous base G in this example as indicated in FIG. 13) at the locus that corresponds to Marker 2. It should be appreciated that, in the illustrative embodiment, the parameters of the global encoder are held constant during the training.

Subsequently, as shown in FIG. 15, the local encoder receives input from a subset of the M markers that are located within a contiguous genomic region (i.e., Chromosome C in this example) and then produces a latent representation encoding local information after accounting for the global latent representation. The local decoder receives the global and local latent representation samples as an input and provides a reconstruction for markers within a given genomic window. To interpret the output of the local decoder, a different threshold may be predefined based on a desired level of accuracy. It should be noted there is a trade-off between accuracy and missingness within the imputed value. For example, by increasing the level of accuracy, a certain marker may be set to missing due to insufficient confidence. For example, a predefined threshold may be set to 0.75. In other words, if the output value for a marker is greater or equal to 0.75, that marker is denoted to have sufficient confidence for an allele call of 1. If, however, the absolute value of the output is less than 0.75, then that marker does not have sufficient confidence for imputation and is set to be missing from that specific genomic region. As such, in the illustrative embodiment, the resulting output markers on Chromosome C is translated to "C G T G . . . T D A I."

It should be noted that FIGS. 16, 17, and 20, which are described further below, utilize the Example Input as input to the global and/or local encoder. Although only one local encoder and one local decoder is shown in FIG. 15, it should be appreciated that, in some embodiments, a system may include multiple local encoders and corresponding local decoders for different genomic region. Each local encoder and decoder are trained to produce and translate a latent representation within a specified genomic region.

The global and local variational autoencoder framework described provides a general method for translation into a universal, platform independent (e.g., marker-independent), latent space. The details of the network structure and the training approach are readily adapted or adjusted to suit any particular application. For instance, convolutional neural networks are used for encoders and/or decoders in order to enforce known spatial structure on hidden layer representations. Generally, optimal performance in testing datasets requires data augmentation, with the augmentation mechanism conditioned upon biological mechanisms and the structure of the populations of interest.

Observed genotypes are supplemented with plausible in silico, predictive crosses to expand the initial finite training set to an effectively infinite training set capable of representing the full diversity of potential haplotype combinations. Input markers can also be masked randomly with missingness patterns observed in the initial dataset. The biological cross augmentation mechanism allows both encoder and decoder neural networks to extrapolate beyond the initial sequenced material to any likely combination of haplotypes, while the augmentation with missing data ensures well-calibrated uncertainty measures within both the latent space and the data reconstructions.

Figure 6:
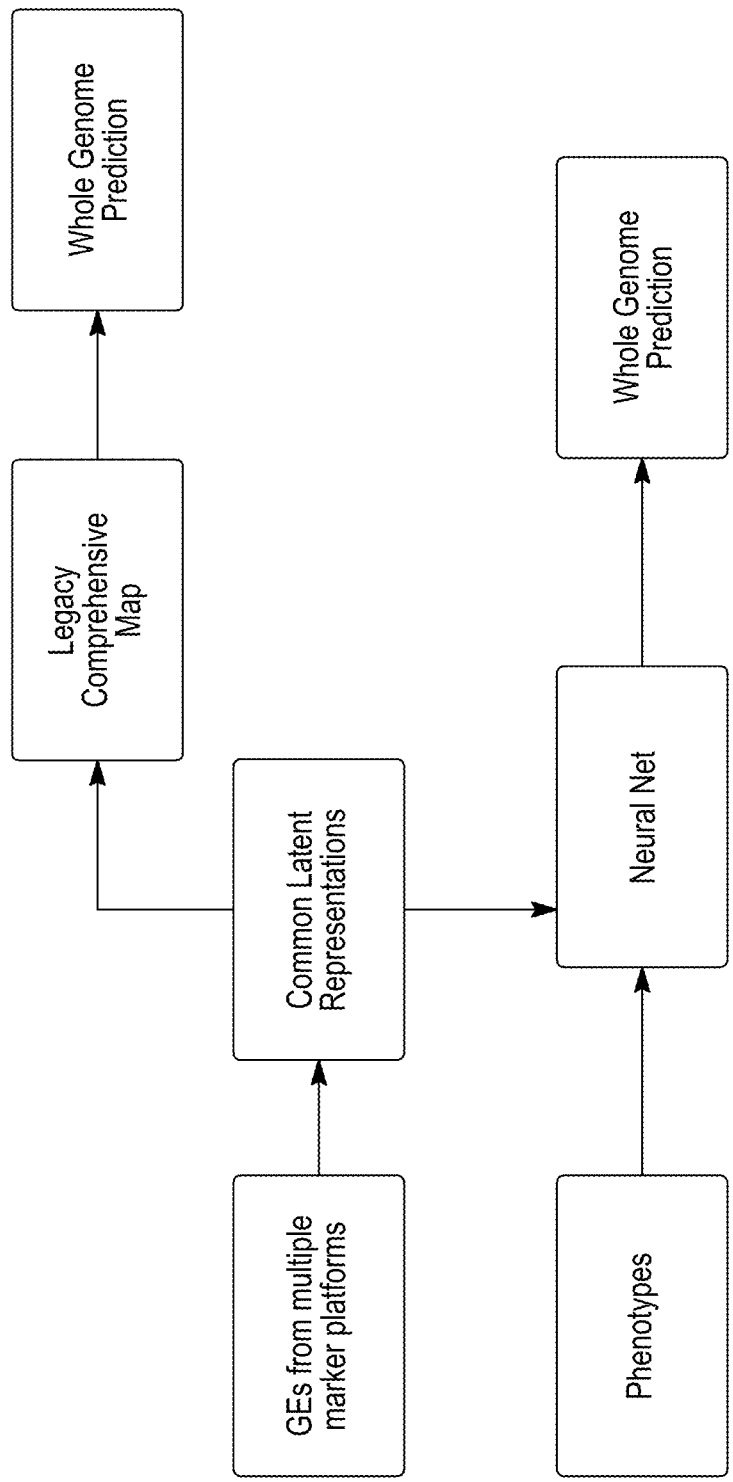
FIG. 6 is a schematic of an example showing the potential applications that can use the imputed information which is based on common latent representations of the underlying marker information, such as genetic elements, from multiple marker platforms.

Referring now to FIG. 6, potential genomic prediction applications based on the latent representations are shown. A unified set of legacy markers can be imputed and then used directly for whole genome prediction based on linear combinations of markers in a legacy comprehensive map. Alternatively, a decoder neural network may be trained to directly translate latent representation to phenotypes of interest. It should be noted that some examples of the potential genomic prediction applications are further described in Examples 1-3 below.

Figure 7:
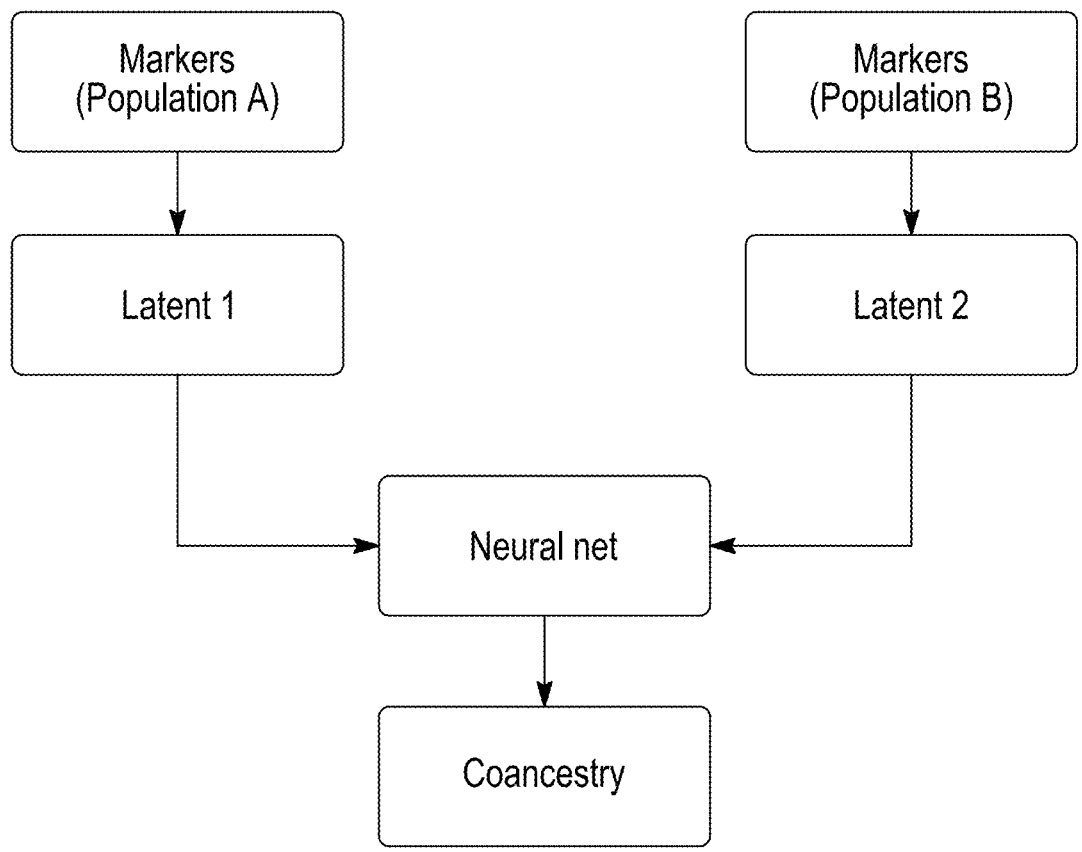
FIG. 7 is a schematic of one example of one method of predicting coancestry between genotypes.

FIG. 7 is an exemplary method of predicting coancestry between genotypes. Latent representations from two genotypes are given to a neural network, which then estimates the coancestry between them. The two genotypes may originate from the same or different populations, and the marker sets may or may not be disjoint. It should be noted that imputing coancestry is further described in Example 6 below.

Figure 8:
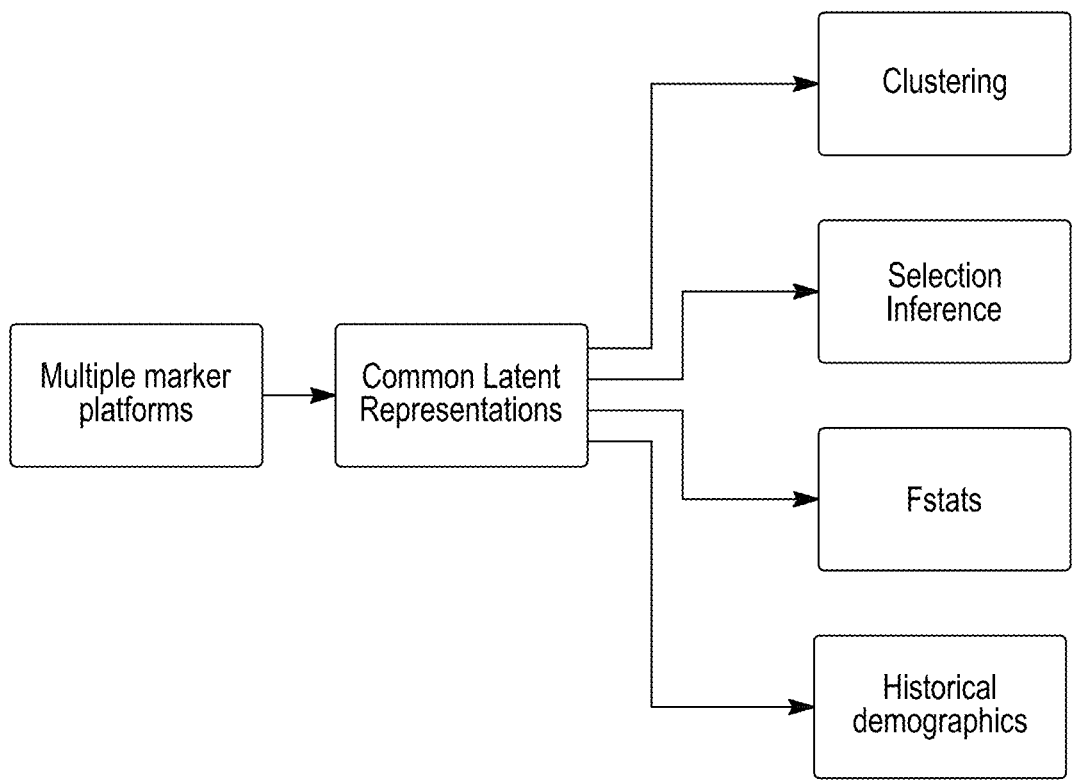
FIG. 8 is a schematic of an example showing that imputed information based on common latent representations of the underlying marker information from multiple marker platforms can be used in clustering, selection inferences, Fstats, historical demographics.

FIG. 8 illustrates that imputed information based on common latent representations of the underlying marker information from multiple marker platforms may be used in clustering, selection inferences, population genetics summaries such as F-statistics, and/or historical demographics.

Figure 9A:
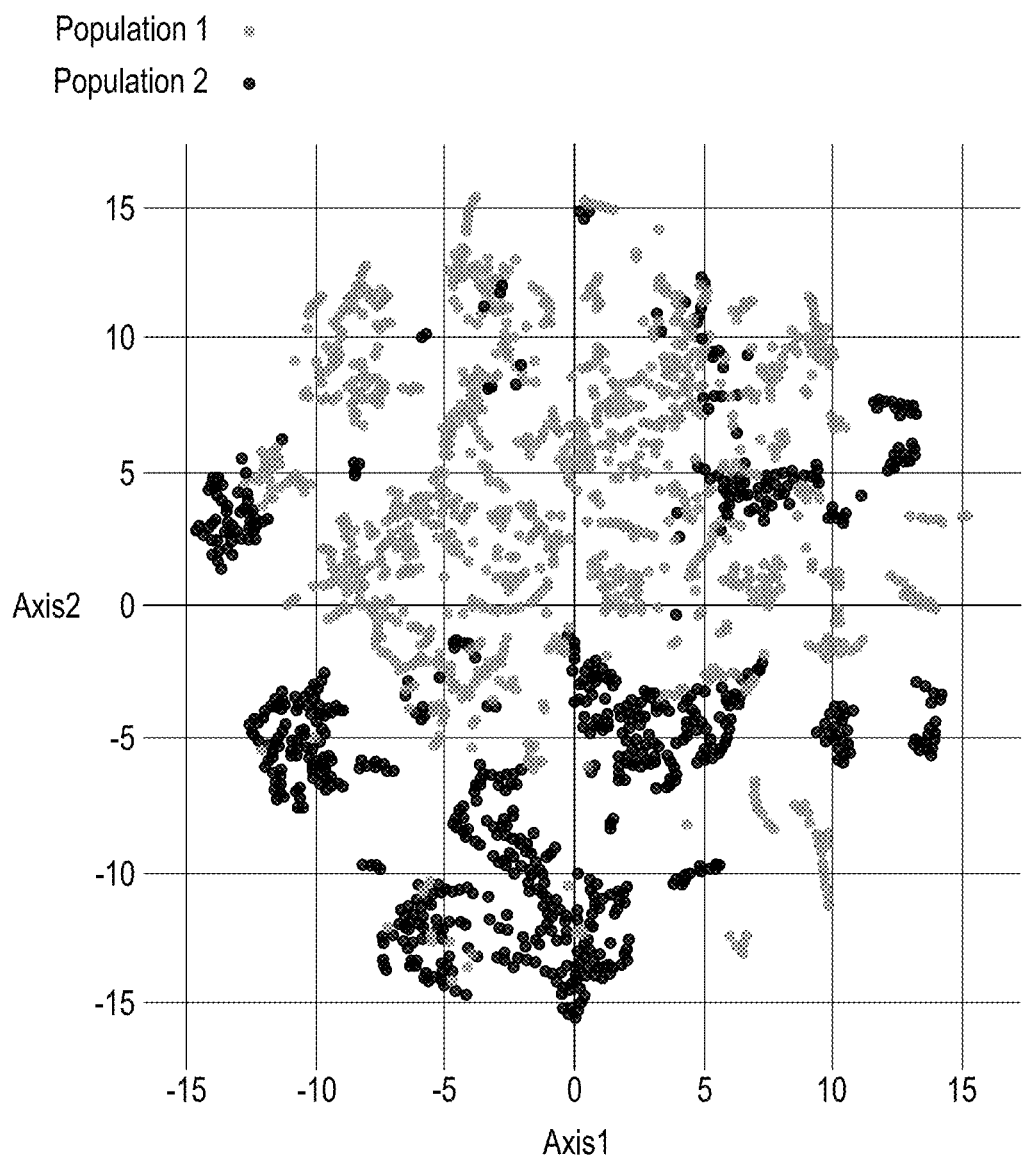
FIG. 9A is an exemplary graph illustrating how the universal translation of the underlying disjoint marker information may lead to robust, genetically-meaningful representations.
Figure 9B:
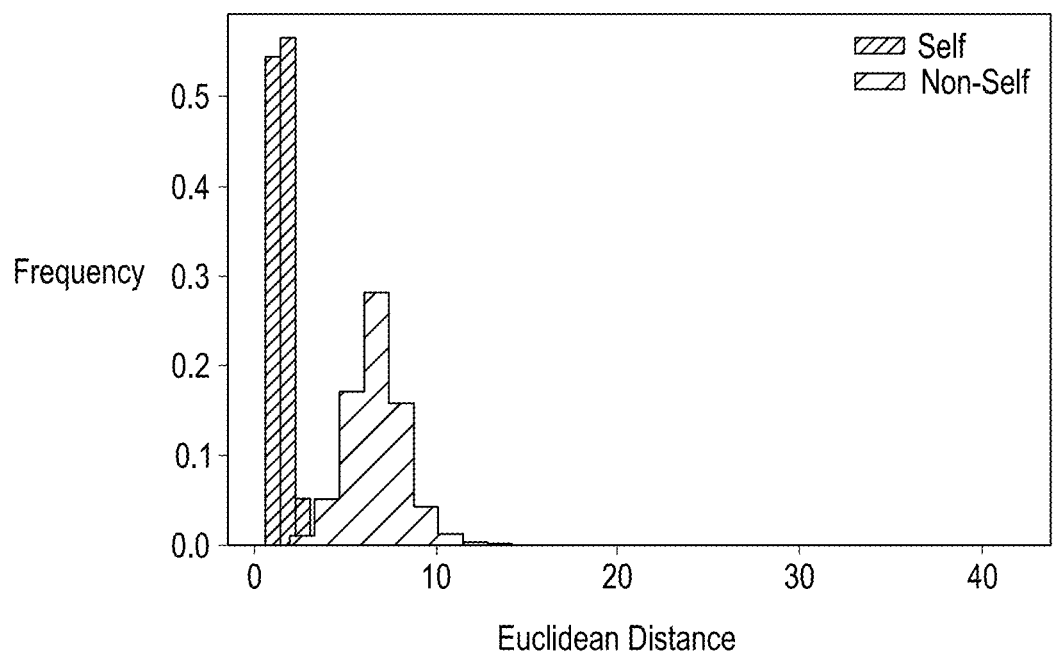
FIG. 9B and FIG. 9C show Euclidean distances of latent representations (FIG. 9B) and Pearson correlations of the latent representations (FIG. 9C).
Figure 9C:
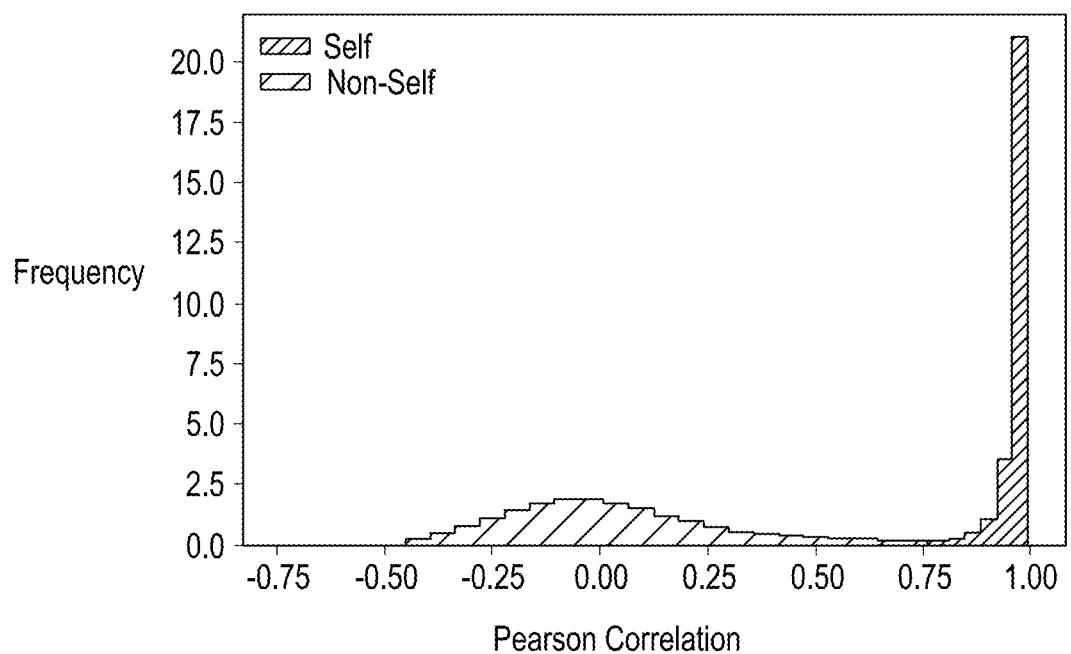

Referring now to FIG. 9, an exemplary graph illustrating how the universal translation of the underlying disjoint marker information may lead to robust, genetically-meaningful representations. Graph A shows a reduced-dimensionality visualization of the global latent space of two populations (i.e., Population 1 and Population 2) with disjoint marker sets. Despite disjointed inputs, the latent representations of a germplasm originated from Population 2 genotyped on the Population 1 marker platform leads to clustering with Population 1's genotyped versions of those inbred lines.

Referring now to Graphs B and C of FIG. 9, Euclidean distances of latent representations (Graph B) and Pearson correlations of the latent representations (Graph C) are shown. As shown in Graph B, the Euclidean distance of latent representations produced by a global encoder with different marker platform inputs of the same breeding line is near zero, which is indicated as "Self" in Graph B. This indicates that the different marker platform inputs of the same breeding line are close to one another. On the other hand, when different marker platform inputs of different breeding lines are used as inputs to the global encoder, the Euclidean distance is significantly greater than zero, which is indicated as "Non-Self" in Graph B.

Similarly, as shown in Graph C of FIG. 9, the Pearson correlation of the latent representations produced by a global encoder with different marker platform inputs of the same breeding line is near one, which is indicated as "Self" in Graph C. On the other hand, when different marker platform inputs of different breeding lines are used as inputs to the global encoder, the Pearson correlation is around zero, which is indicated as "Non-Self" in Graph C. In other words, for distinct genotypes, these measures are significantly different. Graphs B and C of FIG. 9 again illustrate that the encoder is robust to the marker platforms and is relatively invariant to which marker platform is being used as long as the markers are from the same breeding line.

Figure 10A:
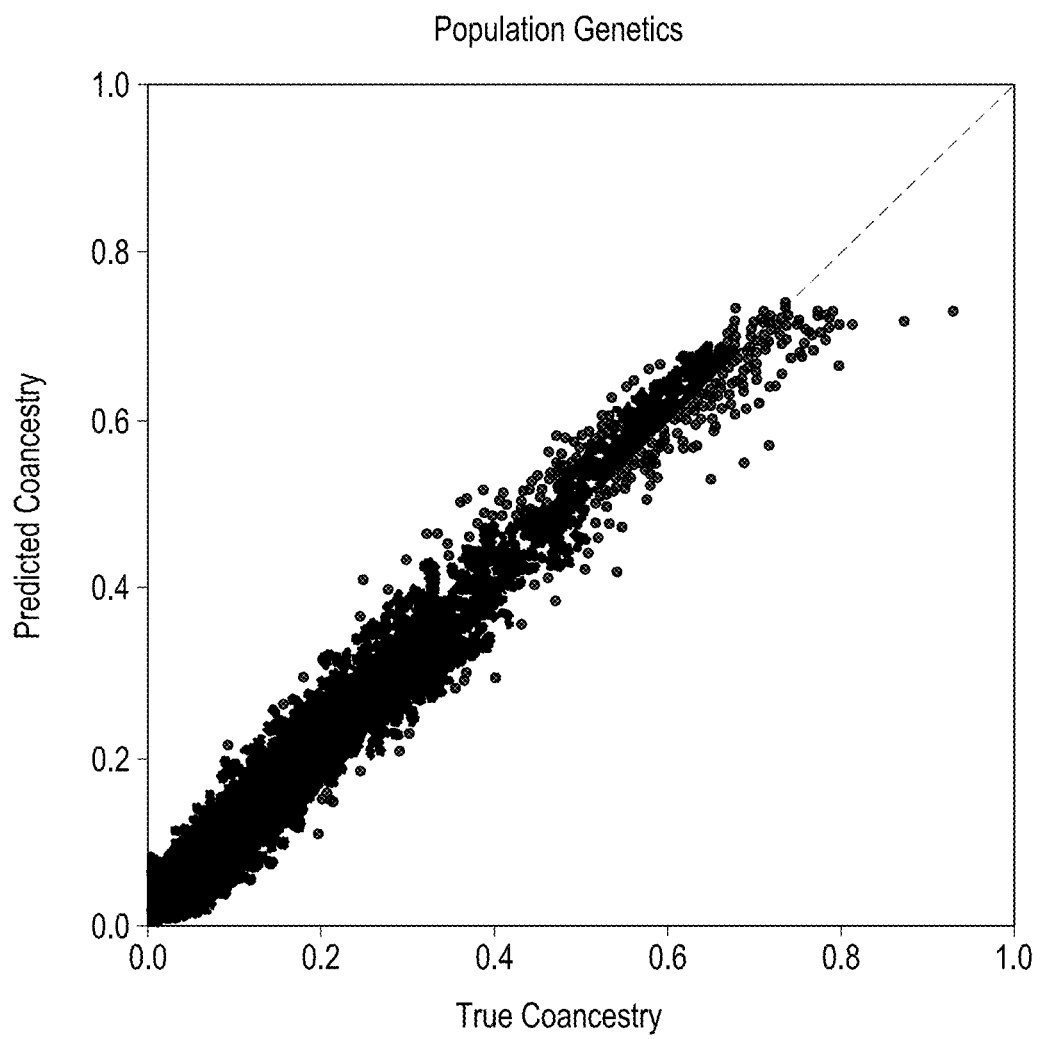
FIG. 10A illustrates how latent representations may be used to predict coancestry of individuals within and between various populations.
Figure 10B:
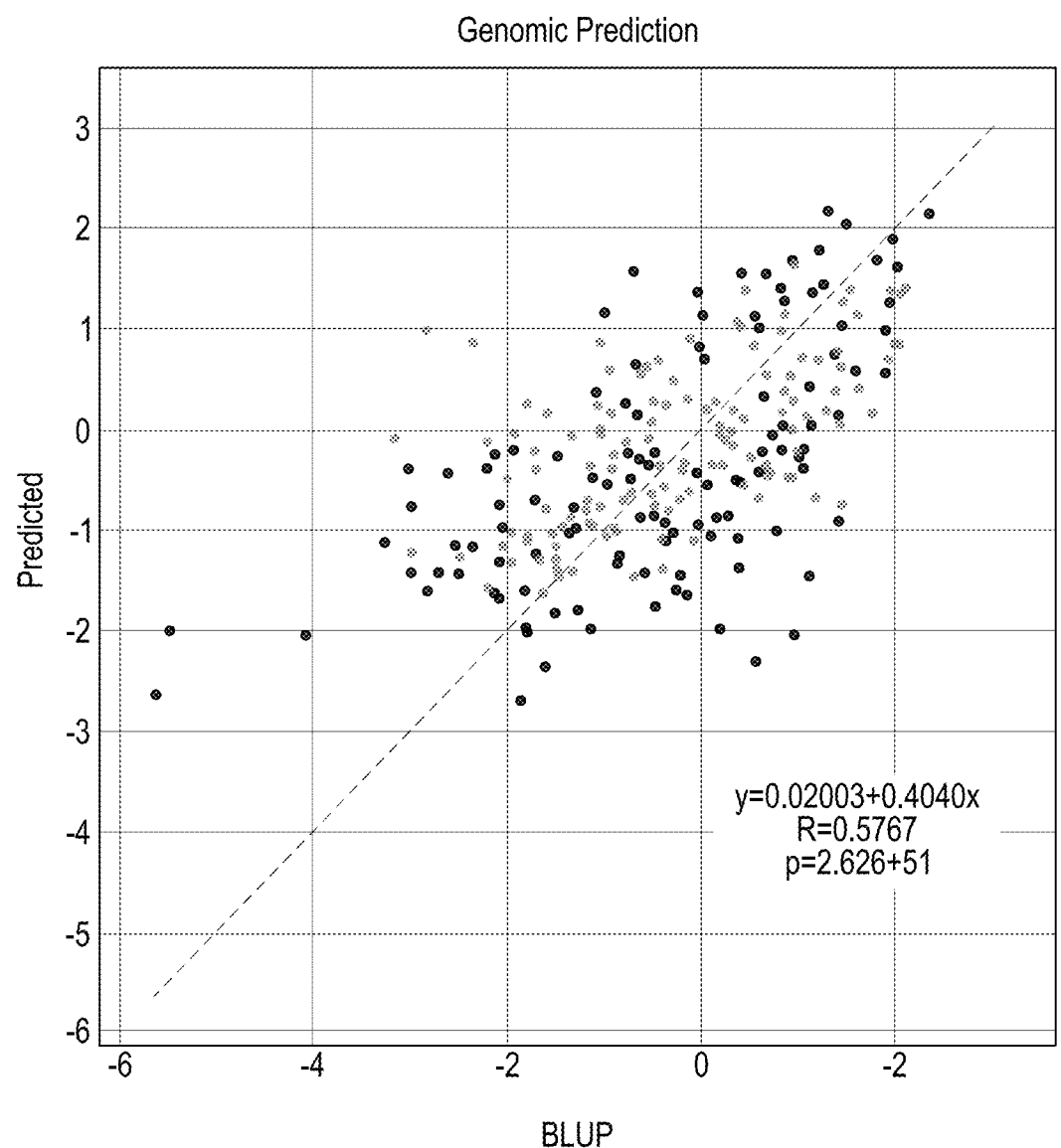
FIG. 10B shows the latent representations may be also used to predict whole-organism phenotypes, as shown here for YIELD within wheat.

FIG. 10 illustrates that latent representations may be used to predict coancestry of individuals within and between various populations as shown in Graph A. Additionally, as shown in Graph B, the latent representations may be also be used to predict whole-organism phenotypes, as shown here for YIELD within wheat.

Figure 11:
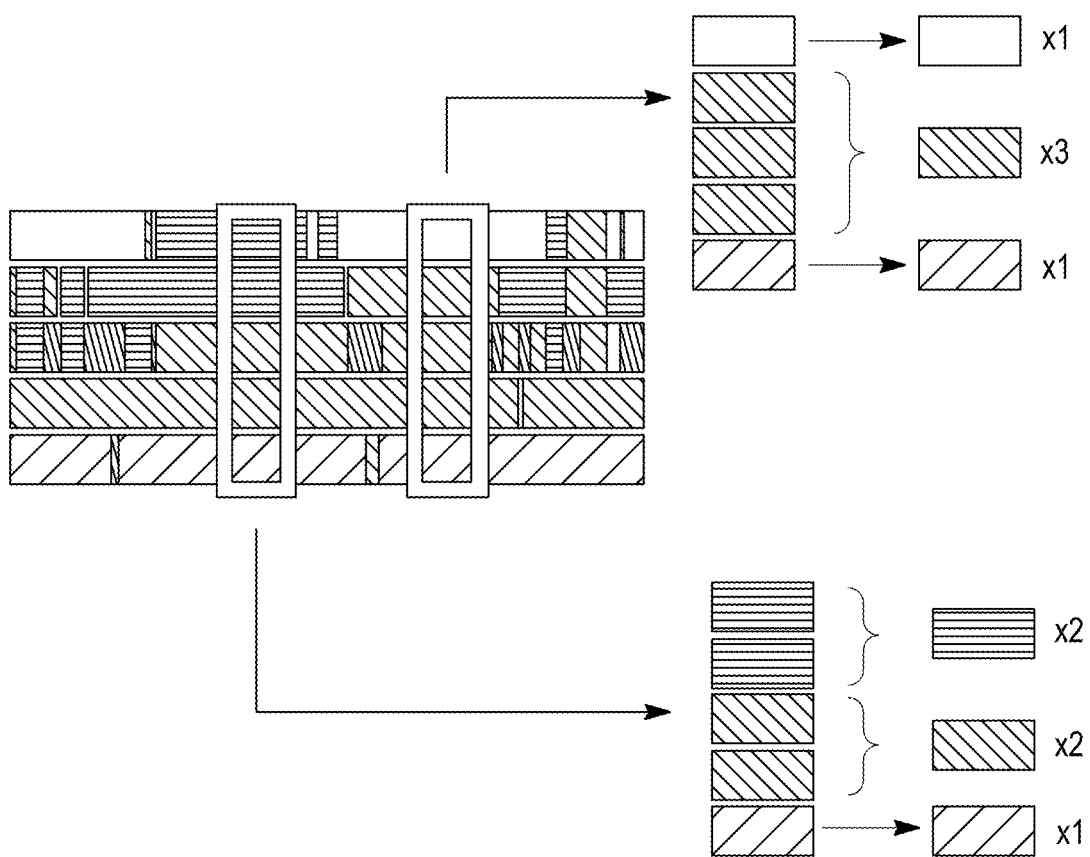
FIG. 11 illustrates embodiments of how haplotype information, which can be imputed based on the universal latent space, may be leveraged for pooling of statistical power in molecular function studies based on replication at the level of the haplotype.

FIG. 11. illustrates embodiments of how haplotype information, which can be imputed based on the universal latent space, may be leveraged for pooling of statistical power in molecular function studies based on replication at the level of the haplotype.

Figure 12A:
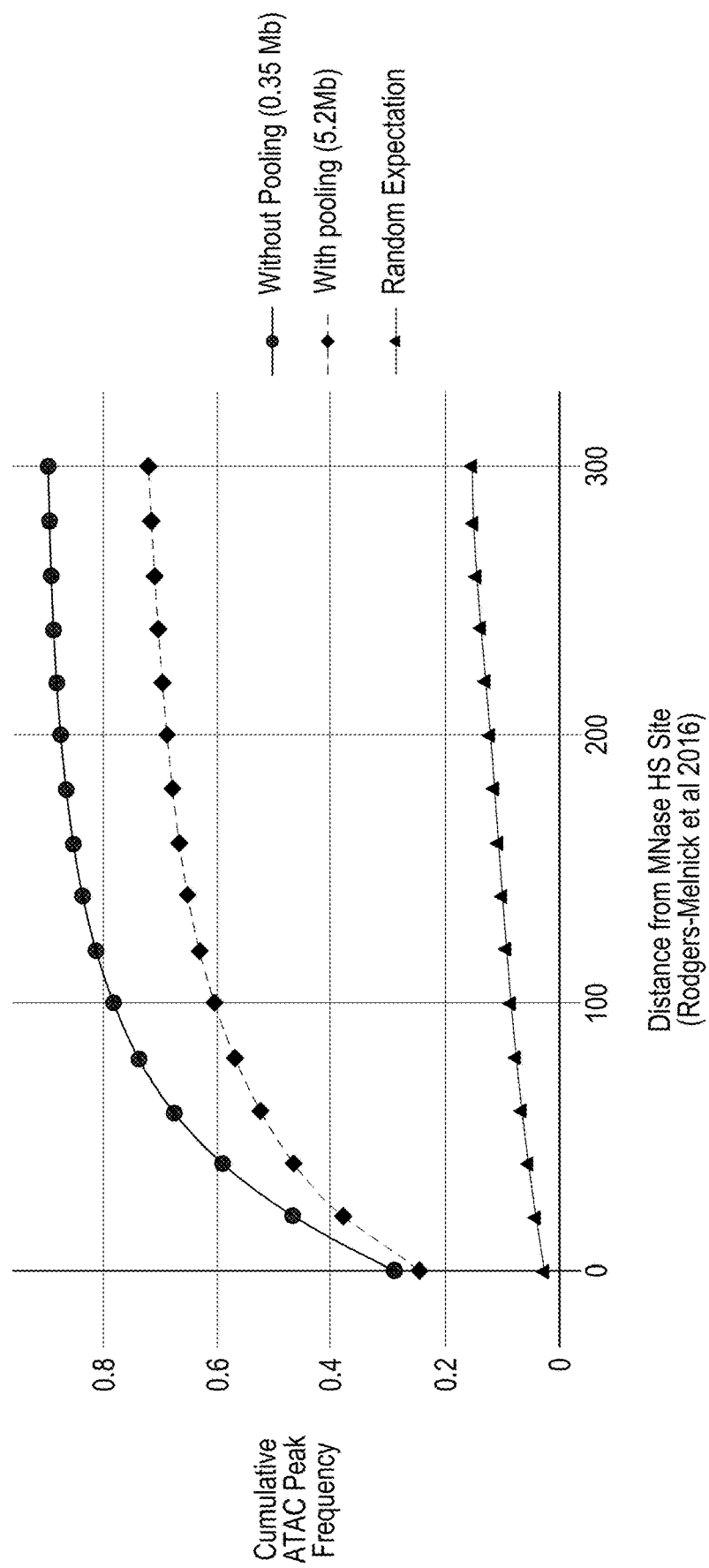
FIG. 12A-12C illustrates how leveraging of the haplotype information through latent representations results in increased statistical power to detect accessible chromatin based on an ATAC-seq assay.
Figure 12B:
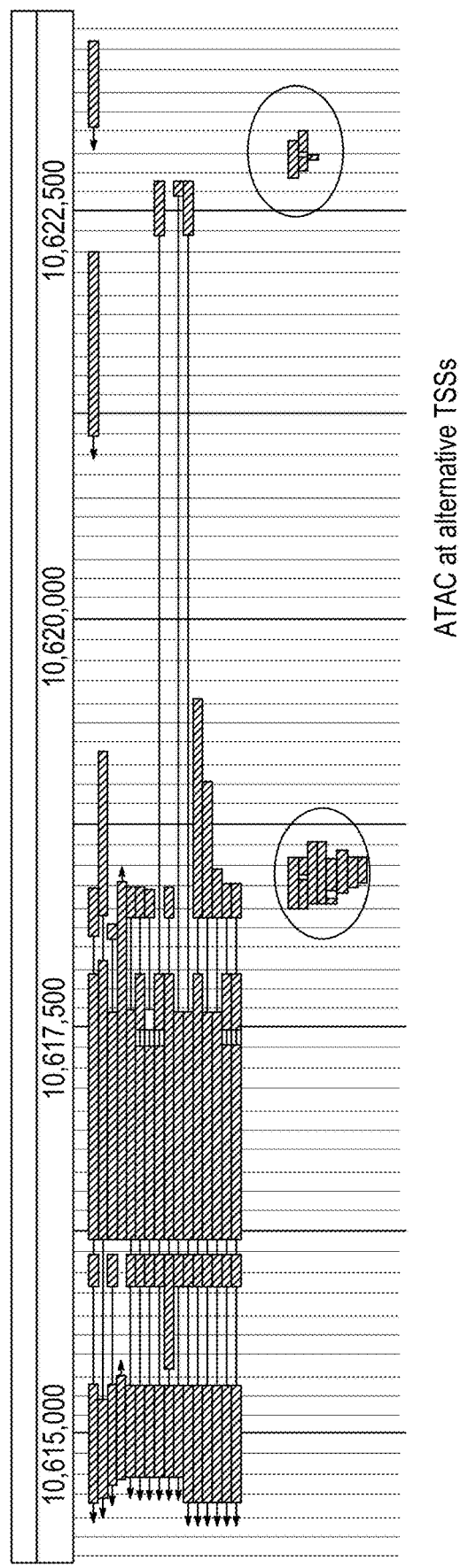
Figure 12C:
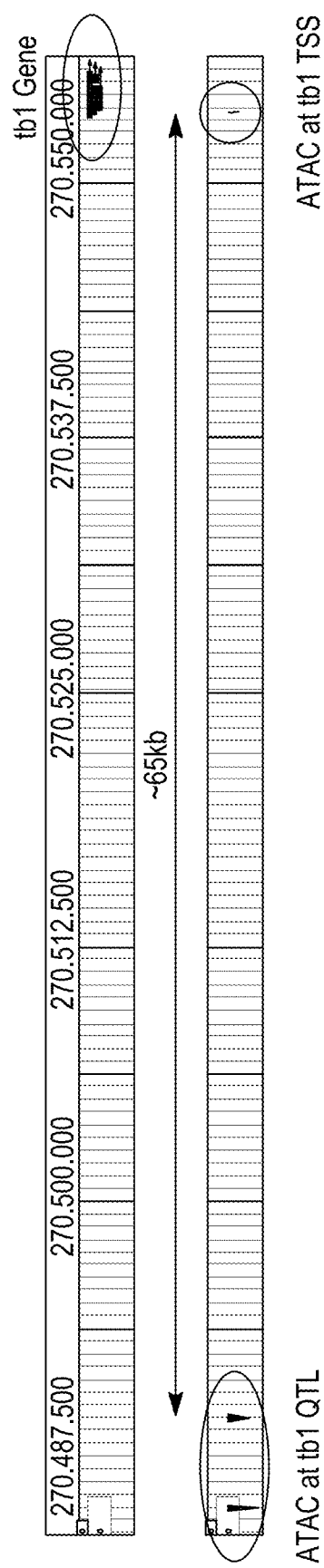

FIG. 12 is an example showing how leveraging of the haplotype information through latent representations results in increased statistical power to detect accessible chromatin based on an ATAC-seq assay. Graph A illustrates the accuracy and power of the haplotype-pooling approach. The location of detected ATAC-seq peaks is compared to those from an independent assay of chromatin accessibility. Peaks detected with or without pooling are both highly enriched within proximity to previously detected peaks relative to random expectation. However, haplotype pooling increases the number of detected peaks by more than an order of magnitude without a substantial loss in accuracy. Graphs B and C illustrate examples of detected peaks using haplotype pooling. Grey lines correspond to tissue peaks that were only detected using haplotype pooling. Graph B illustrates the detection of peaks at alternative TSSs of a single gene, while Graph C illustrates the detection of peaks at a known major QTL in maize that is 65 kb from the nearest protein-coding gene.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

As used herein, the term "haplotype" generally refers to the genotype of any portion of the genome of an individual or the genotype of any portion of the genomes of a group of individuals sharing essentially the same genotype in that portion of their genomes.

As used herein, the term "encoder" generally refers to a network which takes in an input and generates a representation (the encoding) that contains information relevant for the next phase of the network to process it into a desired output format. Generally, the encoder is trained in parallel with the other parts of the network, optimized via backpropagation, to produce representations that are specifically useful for the desired output. For example, a suitable encoder may use a convolutional neural network (CNN) structure, and multi-dimensional encodings or representations are produced. Autoencoders make the encoder generate encodings or representations that are useful for reconstructing its own/prior input and, the entire network may be trained as a whole with the goal of minimizing reconstruction loss.

As used herein, the term "global encoder" generally refers to a network which takes in genome-wide genotypic or phenome-wide phenotypic data as input and generates a representation (the encoding) that contains information relevant for the next phase of the network to process it into a desired output format.

As used herein, the term "local encoder" generally refers to a network which takes in a subset of the genome-wide genotypic or phenome-wide phenotypic data used as input for the global encoder and generates a representation (the encoding) that contains information relevant for the next phase of the network to process it into a desired output format.

As used herein, the term "decoder" generally refers to a network which takes in the output of the encoder and reconstructs a desired output format.

As used herein, the term "global decoder" generally refers to a network which takes in the output of the global encoder and reconstructs a desired output format.

As used herein, the term "local decoder" generally refers to a network which takes in the output of the global encoder and the output from one or more local encoders and reconstructs a desired output format.

Embodiments of the disclosure presented herein provide methods and compositions for using latent representations of data to impute or predict information.

In one embodiment, the imputed or predicted genotypic or phenotypic information is used for genomic prediction, including, but not limited to, whole genome prediction (WGP). Non-limiting examples include but are not limited to those described in WO2016/069078 Improved Molecular Breeding Methods, published May 6, 2016; and WO2015/100236 Improved Molecular Breeding Methods, published Jul. 2, 2015, each of which is incorporated herein by reference in their entirety. For example, imputed genotypic or predicted phenotypic information and optionally with a biological model such as a biological model that includes gene networks, biochemical pathways, physiological crop growth model (CGM) or combinations thereof, may be used to predict phenotype or trait performance for individuals under various types of environmental conditions. Exemplary types of environmental conditions include but are not limited to increased or decreased water supply in soil, temperature, plant density, and disease or pest stress conditions. One or more individuals having a desired predicted phenotype or trait performance may be produced, grown or crossed with itself or another individual to generate offspring with a desired predicted phenotype or trait performance. Accordingly, in one embodiment, the methods are used to select individuals for use in a breeding program. In another embodiment, one or more individuals having an undesired predicted phenotype or trait performance may be culled from a breeding program.

In another embodiment, imputed molecular and whole plant information may be used to predict phenotype or trait performance for individuals.

In one embodiment, a universal method of parametrically representing genotypic or phenotypic association data from a training data set obtained from a population or a sample set to impute genotype and/or phenotype in a test data obtained from a test population or a test sample data is provided herein.

Any population of interest may be used with the methods and compositions described herein. While the methods disclosed herein are exemplified and described primarily using plant populations, the methods are equally applicable to animal populations, for example, non-human animals, such as domesticated livestock, laboratory animals, companion animals, etc.

The animal may be a poultry species, a porcine species, a bovine species, an ovine species, an equine species, or a companion animal, and the like. Accordingly, in some embodiments, the population is a population of plants or animals, for example, plant or animal populations for use in a breeding program. In some examples, the one or more populations include plant populations of inbred plants, hybrid plants, doubled haploid plants, including but not limited to F1 or F2 doubled haploid plants, offspring or progeny thereof, including those from in silico crosses, or any combination of one or more of the foregoing. Any monocot or dicot plant may used with the methods and compositions provided herein, including but not limited to a soybean, maize, sorghum, cotton, canola, sunflower, rice, wheat, sugarcane, alfalfa tobacco, barley, cassava, peanuts, millet, oil palm, potatoes, rye, or sugar beet plant. In some embodiments, the genotypic data and/or phenotypic data is obtained from a population of soybean, maize, sorghum, cotton, canola, sunflower, rice, wheat, sugarcane, alfalfa tobacco, barley, cassava, peanuts, millet, oil palm, potatoes, rye, or sugar beet plants.

In some examples, the genotype of interest is associated with a desirable trait of interest and/or the absence of undesirable trait of interest.

Plant or animal populations or one or more members thereof that are imputed or predicted to have a desired genotype of interest or phenotype of interest may be selected for use in a breeding program. For example, the population or one or more members may be used in recurrent selection, bulk selection, mass selection, backcrossing, pedigree breeding, open pollination breeding, and/or genetic marker enhanced selection. In some instances, a plant having the imputed or predicted desirable genotype of interest or phenotype of interest may be crossed with another plant or back-crossed so that the imputed or predicted desirable genotype may be introgressed into the plant by sexual outcrossing or other conventional breeding methods.

In some examples, plant having the imputed or predicted desirable genotype of interest or phenotype of interest may be used in crosses with another plant from the same or different population to generate a population of progeny. The plants may be selected and crossed according to any breeding protocol relevant to the particular breeding program.

In other examples, plant having the imputed or predicted undesirable genotype of interest or phenotype of interest may be counter-selected and removed from a breeding program.

In some aspects, the method includes generating a universal continuous global latent space representation by encoding discrete or continuous variables derived from a genome-wide genotypic or phenome-wide phenotypic association training data into latent vectors through a machine learning-based global variational autoencoder framework. In some aspects, the global latent space is independent of the underlying genotypic or phenotypic association. In some aspects, the method includes generating a local latent representation by encoding a subset of the discrete or continuous variables derived from the genotypic or phenotypic association training data set into latent vectors through a machine learning-based local variational autoencoder framework, where the local latent space is generated with inputs from the local variational autoencoder and the global variational autoencoder. In some aspects, the method includes decoding the global latent representation and the local latent representation by a local decoder, thereby imputing or predicting the genotype or phenotype of the test data by the combination of the decoded global latent representation and the local latent representation.

In some aspects, the genotypic association data includes a collection of genotypic markers or single nucleotide polymorphisms (SNPs) from a plurality of a genetically divergent population. The subset of the discrete variables may be a plurality of single nucleotide polymorphisms (SNPs) localized to a segment of the chromosome. In some aspects, the variational autoencoder is based on a neural network algorithm. In some aspects, the phenotype that is imputed or predicted in the test data or test sample is predicted yield gain. In some aspects, the imputed or predicted phenotype in the test data or test sample is root lodging, stalk lodging, brittle snap, ear height, grain moisture, plant height, disease resistance, drought tolerance, or a combination thereof. In some aspects, the imputed or predicted genotype that is in the test data or test sample is a plurality of haplotypes. In some aspects, the local decoder imputes local high-density (HD) SNPs.

In some aspects, the genotypic association data is obtained from populations of plants derived from two or more breeding programs, where the breeding programs do not comprise an identical set of markers or single nucleotide polymorphisms (SNPs) corresponding to the genotypic association data. In some aspects, the local decoder imputes local high-density (HD) SNPs of one population based on the decoding of genotypic association data of another population. In some aspects, the local decoder imputes haplotypes for one population based on the decoding of genotypic association data of another population. In some aspects, the local decoder imputes or predicts a molecular phenotype including but not limited to gene expression, chromatin accessibility, DNA methylation, histone modifications, recombination hotspots, genomic landing locations for transgenes, transcription factor binding status, or a combination thereof. Gene expression may include a change in the activity or level of expression of transcripts, genes, or other transcribed nucleotide sequences including those global (genome-wide) or local or a subset thereof, a population (subset) of genes, or a gene of interest. In some aspects, the local decoder imputes or predicts population coancestry for one or more of the test populations.

Also provided herein in an embodiment is a universal method of parametrically representing genotypic or phenotypic association data from a training data set obtained from a population or a sample set to infer a characteristic of interest, e.g. a desirable characteristic, in test data obtained from a test population or a test sample data. In some aspects, the method includes generating a universal continuous global latent space representation by encoding discrete or continuous variables derived from a genome-wide genotypic association or phenome-wide phenotypic training data into latent vectors through a machine learning-based global variational autoencoder framework, where the global latent space is independent of the underlying genotypic or phenotypic association. In some aspects, the method includes decoding the global latent representation by a global decoder, thereby inferring the characteristic of interest, e.g. a desirable characteristic, of the test data by the decoded global latent representation.

In some aspects, the characteristic of interest, e.g. a desirable characteristic, is without limitation coancestry determination of two or more populations of plants or predicting yield gain or an agronomic phenotype of interest. In some aspects, the variational autoencoder is based on a neural network algorithm.

Also provided herein is a universal method of developing universal representation of genotypic or phenotypic data that includes receiving by a first neural network one or more training genotypic or phenotypic data, where the first neural network includes a global variational autoencoder. In some aspects, the method includes encoding by the global encoder, the information from one or more training genotypic or phenotypic data into latent vectors through a machine-learning based neural network training framework. In some aspects, the method includes providing the encoded latent vectors (generated from other genotypic or phenotypic data) to a second machine-learning based neural network, where the second neural network includes a decoder. In some aspects, the method includes training the decoder to learn a prediction or imputation of a genotype or phenotype of interest based on an objective function for the encoded latent vectors. In some aspects, the method includes decoding by the decoder the encoded latent vector for the objective function. In some aspects, the method includes providing an output for the objective function of the decoded latent vector.

Also provided herein is a method of selecting an attribute of interest based on genotypic or phenotypic data. In some aspects, the method includes receiving by a first neural network one or more training global genotypic or phenotypic data, where the first neural network includes a global variational autoencoder. In some aspects, the method includes encoding by the global variational autoencoder, genotypic or phenotypic information from one or more training genotypic or phenotypic data into latent vectors. In some aspects, the method includes training the global variational autoencoder using the latent vectors to learn underlying genotypic or phenotypic correlations and/or relatedness. In some aspects, the method includes receiving by a second neural network one or more training local genotypic or phenotypic data, where the local genotypic or phenotypic data is directed to a subset of global genotypic or phenotypic data that corresponds to a certain attribute of interest, where the second neural network includes a local variational autoencoder. In some aspects, the method includes encoding by the local variational autoencoder, the genotypic or phenotypic information from the one or more training local genotypic or phenotypic data into latent vectors. In some aspects, the method includes training the local variational autoencoder using the latent vectors to learn underlying genotypic or phenotypic correlations and/or relatedness for the attribute of interest. In some aspects, the method includes providing the encoded latent vectors from the global variational autoencoder and/or local encoder to a third neural network, where the third neural network includes a decoder. In some aspects, the method includes training the decoder to predict the attribute of interest for the encoded latent vectors from the global variational autoencoder and/or the local variational autoencoder using a pre-specified or learned objective function. In some aspects, the method includes decoding by the decoder, the encoded latent vectors for the objective function. In some aspects, the method includes providing an output for the objective function of the decoded latent vector.

The decoder may include one or more decoders. In some aspects, the decoder is a local decoder. In some aspects, the decoder is a global decoder and decodes the encoded latent vectors from the global encoder. In some aspects, the global training genotypic data includes markers across the genome. In some aspects, the local genotypic data is from a specific chromosomal genomic region of interest or allele. In some aspects, the method includes training the global encoder and decoder simultaneously.

In some aspects, the local attribute may include without limitation SNPs, alleles, markers, QTLs, gene expression, phenotypic variation, metabolite level, or combinations thereof. In some aspects, the encoder may be an autoencoder. In some aspects, the autoencoder is a variational autoencoder.

In some aspects, the training genotypic data includes without limitation SNPs or indels sequence information. In some aspects, the training genotypic or phenotypic data includes sequence information from in silico crosses. In some aspects, the encoder weights are updated relative to a reconstruction error so that the training genotypic or phenotypic data information is separated within the latent space. In some aspects, the decoder is trained on existing genotypic or phenotypic data.

Also provided herein is a computer system for generating genotypic or phenotypic data determinations. In one embodiment, the system includes a first neutral network that includes a variational autoencoder configured to encode genotypic or phenotypic information from one or more training genotypic or phenotypic data into universal latent vectors, where the encoder has been trained to represent genotypic or phenotypic associations through a machine-learning based neural network framework and a second neural network includes decoder configured to decode the encoded latent vectors and generate an output for an objective function.

In an embodiment, a computer system, includes one or more computer programs or other software elements or special programmable instructions, or computer-implemented logic that is configured to parametrize genotypic data, phenotypic data, association data or a combination thereof into latent space as described herein. In an embodiment, the computer system is connected, via a network, to one or more data resources.

EXAMPLES

The present invention is illustrated by the following examples. The foregoing and following description of the present invention and the various examples are not intended to be limiting of the invention but rather are illustrative thereof. Hence, it will be understood that the invention is not limited to the specific details of these examples.

Example 1

Marker Imputation Across Disparate Germplasm and Marker Platforms

The maize germplasm collections that originated from distinct closed breeding programs were used for this analysis. These distinct germplasm populations were originally genotyped on disparate marker platforms with a small minority (about 2%) of markers in common between them. Whole genome sequencing and exome capture sequencing efforts provided high density single nucleotide polymorphism (SNP) markers for a smaller subset (~1200 breeding program A, ~2500 breeding program B) of the available inbred lines, and these were mapped to a maize reference genome. A subset of approximately 350,000 high density markers were identified to be in common between the two high density marker sets, and these were selected to provide a measure of reconstruction error that would span both legacy sets of germplasm. Approximately 7,000 SNPs were also identified in the high density data that were used as production markers in one or the other breeding programs. These markers were selected to augment the production marker input and output during training of an autoencoder neural network. A subset of markers was set aside to serve as a basis for scoring the accuracy of cross-breeding program imputation when markers are completely disjoint during training.

As discussed above, the autoencoder neural network may be trained to translate production markers from different populations of germplasm into a universal, platform independent (e.g., marker-independent), latent space. To do so, the training process involves three steps, as described above with regard to FIGS. 5A and 5B. Steps 1 and 2 establish a common latent space between the two sets of germplasm at the global and local scales, while Step 3 provides a decoder to translate from the common latent space to the union of legacy production markers. In this example, in order to augment the training set beyond the ~3700 inbred lines available with high density data, synthetic F1 doubled haploids were simulated based on in silico crosses between pre-specified pairs of inbred lines from the high-density genotyped training set.

In step 1, the global encoder was trained with an input that includes the union of legacy breeding program markers. In the illustrative embodiment, markers are coded as homozygous for allele A, homozygous for allele B, or missing. Marker invariant latent representation was enhanced through a randomized input scheme. For each input within each minibatch, the set of production markers was randomly chosen to be those from breeding program A, those from breeding program B, or those from the union based on production marker augmentation from the high density SNPs. The dimension of the global latent space was set to 32, so that 32 real numbers were sampled based on the global encoder output and sent to the global decoder. The global decoder then translated the latent input into a reconstruction of the subset of high density SNPs (10,000) chosen for global training, and the loss was calculated based on the reconstruction error and the KL-divergence between the latent representation and the prior of univariate Gaussians.

In Step 2, local encoders and high-density local decoders were trained within 10 cM bins across the breeding program A maize genetic map. The input to local encoders was restricted to the union of both the breeding programs A and B production SNPs within the chromosome containing the 10 cM bin of interest. Randomization of the input SNP set proceeded as described in Step 1. The size of each local latent space was set to 16, with the Gaussian parameterization otherwise identical to that of the global encoder. Each local decoder received as input the sampled latent output of the local encoder, along with the sampled latent output of the global encoder. In this example, the global encoder weights were not updated during the local training process. In Step 3, the local decoder translated the combined global and local latent representations into a reconstruction of the full set of high density SNPs located within each 10 cM region of interest. The reconstruction error combined with the KL-divergence from the local latent Gaussian priors were used to calculate the loss.

The weights of the global and all local encoders were frozen, and new local production marker decoders were trained for each 10 cM bin, with the input of each local production marker decoder corresponding to those of the high-density marker decoder described in Step 2. The loss for this step was only dependent on the reconstruction error of the combined set of production markers, and loss was only accumulated for production markers that were non-missing for a given inbred line. The randomization scheme for the input markers followed that described in Steps 1 and 2.

Following training, imputation accuracy and characterization of the latent space was assessed on a pre-specified held-out, randomly-selected testing set spanning the legacy organizations. Euclidean distances of latent vectors for the same inbred line encoded by the disjoint marker sets of the legacy organizations were clustered near zero, while distances for non-identical lines formed a Gaussian distribution with a mode around 8. Pearson correlations for the latent vectors of the same inbred line with disjoint marker sets clustered near 1, compared to a distribution around 0 for non-identical lines. Testing accuracy of imputed high density SNPs ranged from 97.4% across 100% of high-density SNPs when no confidence cutoff was imposed to 99.1% accuracy across 93.3% of SNPs when a moderate threshold of 0.9 was used to 99.7% accuracy across 86.1% of SNPs when a high threshold of 0.99 was used.

Imputation accuracy for production SNPs varied with the breeding programs and the disjointedness of the training regime for the associated markers. Across all testing germplasm and markers—at the chosen moderate threshold of 0.9, imputation accuracy was 99.2% and covered 91.5% of the union of breeding program B and breeding program A production markers. Within breeding program A, testing accuracy for breeding program B production markers that were augmented during training was 98.5%, with 88.1% imputed. The breeding program A testing accuracy for breeding program B markers that were left completely disjoint during training was 96.6%, with 85.4% of these disjoint markers imputed. For breeding program b, testing accuracy for breeding program A production markers augmented during training was 99.3%, with 93% of markers imputed. For breeding program B non-augmented markers, the accuracy was 97.5% with 90% of markers imputed.

Thus, this example demonstrates that by employing machine-learning based variational autoencoder framework for global and local encoding followed by decoding successfully imputes marker data across disparate breeding programs that do not necessarily share substantially the same genotypic association data set (e.g., marker or sequence information). This example also demonstrates that such imputation efficiency can accelerate breeding including for example selection of breeding pairs, predicting hybrid performance such as yield, lodging and other desirable characteristics.

Example 2

Haplotype Imputation from Latent Space

Haplotypes—generally referred to herein as linked sets of co-segregating markers in a population—provide a useful means for visualizing genetic variation and imputing functional information to regions of identical sequence across a given population. Using the 350,000 high-density markers in common between breeding program B and breeding program A germplasm—as described in Example 1—a common haplotype framework was established between the breeding program datasets by assigning groups of near identical sequence within each specified region to common haplotypes. Such regions have been defined on both genetic (e.g. 1 cM) and physical (e.g. 1 Mb) maps, including haplotypes at the individual gene level. At the 1 cM genetic scale, regions with high density SNP identity of at least 97% were considered to have common haplotypes. However, generalization of the haplotype framework to inbred lines without high density markers required the use of the genotypic information captured within the global and local latent representations.

Following the training of the cross-breeding programs global and local encoders described in Example 1, local haplotype decoders were trained within each haplotype bin. As input, each haplotype decoder received the global latent representation and the local latent representation for the region containing the haplotype bin. The output layer of each decoder was set to the same size as the total number of haplotypes in the bin, and the output activation function was specified such that the sum of all scores for all haplotypes in a region would sum to 1. That is, the score for any haplotype could be interpreted as a probability. Training proceeded using the same input randomization and in silico crossing scheme described in Example 1. The definitions of training and testing sets were also maintained from the training of global and local encoders in Example 1.

Figure 16:
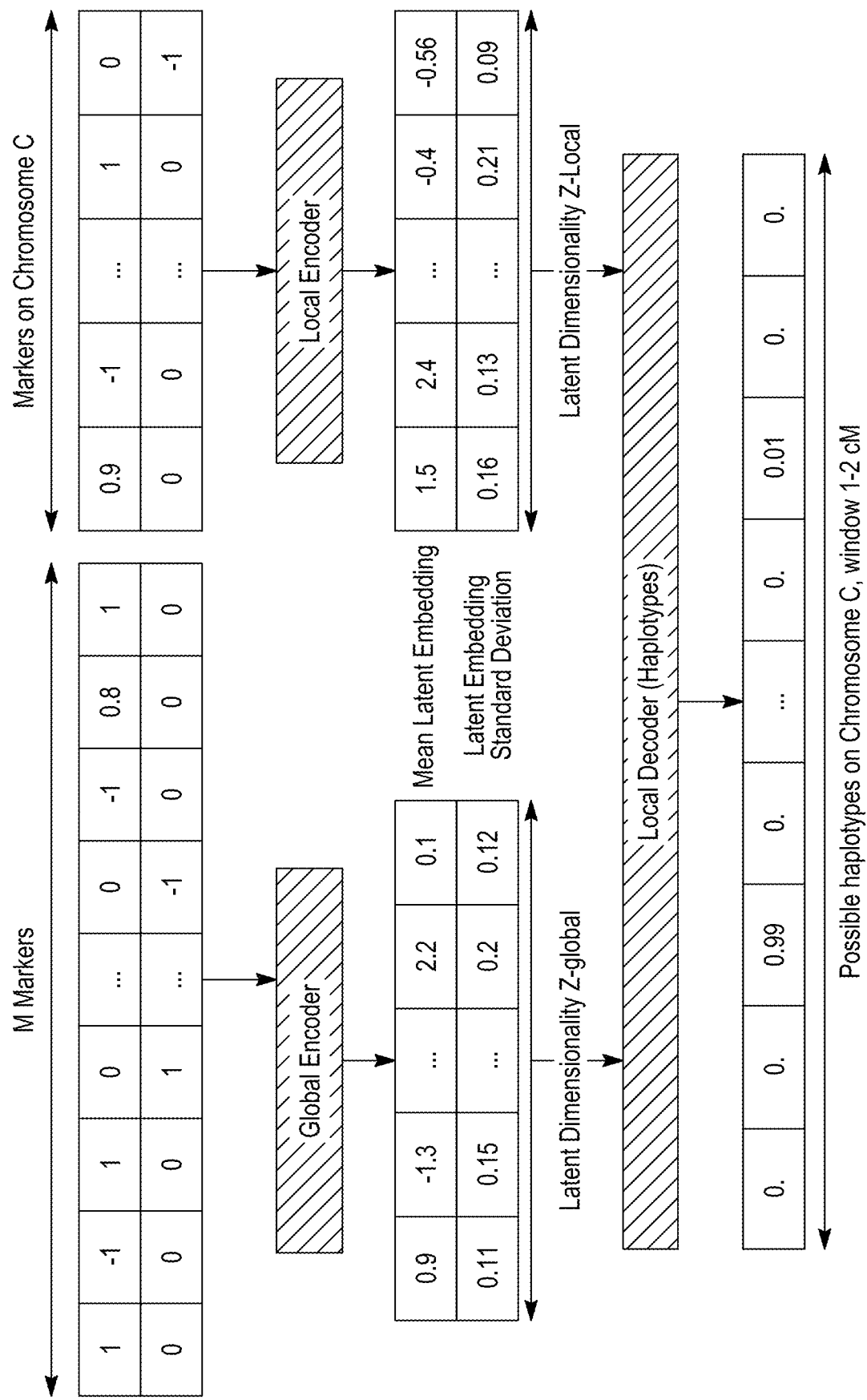

For example, FIG. 16 illustrates example input and output for a haplotype decoder. Once the global and local encoders are trained as described in Example 1, their parameters are held constant. The local decoder is then trained to predict the probability of each haplotype within a genomic bin that is a subset of the local encoder's range (i.e., Chromosome C in this example). Each column of the local decoder output is associated with a particular haplotype, and a value in each column indicates a probability that the respective haplotype is present within the specified bin on Chromosome C. For example, 0.99 in a third column indicates that the probability that the bin from 1-2 cM on Chromosome C has Haplotype 3 is 0.99.

Characterization of haplotype imputation accuracy was performed for both breeding program A and breeding program B testing germplasm following the completion of decoder training. At the chosen haplotype calling threshold of 0.9, 77.3% of all haplotype bins within breeding program A could be imputed with 96% accuracy, while 86.9% of breeding program B haplotypes were able to be called with 98.3% accuracy. For both breeding programs (A and B), a particular breeding line, which had haplotypes well represented within the training data, performed much higher than average both in terms of total imputation frequency and accuracy. Loss of accuracy was primarily due to older inbreds, inbreds from different sources outside the breeding programs, and inbreds with a low number of markers.

Thus, this Example demonstrates that haplotypes for a test breeding population can be imputed based on latent representations of the underlying genotypic data (e.g., high-density markers) through global encoding, local encoding and decoding using variational autoencoding framework.

Example 3

Imputation of Haplotypes in Multiple Crops

Haplotype frameworks were initiated with breeding program A germplasm for crops outside of corn, including the monocot grass rice and the dicot legume soybean. Haplotype sets were constructed using methods described in Example 2, following whole genome sequencing and characterization of high-density SNP variation within representative lines originating from the breeding programs of each crop. After construction of the haplotype frameworks, imputation of the haplotypes was initiated on non-sequenced members of each species using the inference from global and local latent spaces.

Approximately 700 production markers within rice and 2000 production markers within soy were collected to serve as inputs for all global and local encoders. Prior to training, test sets were defined such that they would only be used for characterization of imputation accuracy. Sets of plausible crosses between breeding lines were also collected to allow for data augmentation during training with in silico crosses between observed lines.

The global encoders were first trained with variational autoencoding objectives, using the same production markers for both the input to the global encoders and the output from the global decoders. The global decoders received sampled latent vectors from the global encoders during training. The dimensionality of the global latent space was set to 32 for each species, and the objective function for the global autoencoder framework included reconstruction error terms for the production markers and unit-Gaussian KL-divergence penalties for the latent space. Both observed and in silico crosses were sampled during training, in addition to random dropout of markers to simulate a wide sample of missingness scenarios.

Following the completion of global encoder and decoder training, training of the local encoders and local haplotype decoders was initiated. Local encoders and decoders were trained simultaneously, with each local encoder spanning a subsection of a single chromosome and each local decoder spanning a single haplotype bin within the physical span of the given local encoder. Sampling of in silico crosses and random dropout of markers proceeded as in the training of the global encoder. The input to each local encoder consisted of the production markers from only its assigned chromosome, while the input to the local decoder included a sampled global latent vector from the global encoder and a sampled local latent vector from the local encoder. As mentioned in Examples 1 and 2, the weights of the global encoder were not updated during training of the local encoders and decoders. The output of each local decoder was set to the size of the number of haplotypes within the given bin, with the sum of all haplotype scores for an example summing to 1, as in Example 2. The objective function for the local encoders and decoders consisted of the reconstruction error for the imputed haplotypes and the KL-divergence between the unit Gaussian priors and the distribution of the local latent space.

Following the completion of all global and local neural networks, haplotype imputation accuracy was assessed on the testing sets of each crop species. Within rice, a moderate threshold of 0.75 permitted haplotype imputation over an average of 81% of each genome with an accuracy of 97.5% using its ~700 markers. The same threshold in soy with ~2000 markers led to a testing accuracy of 96.8% over an average of 79.8% of the genome.

Thus, this Example demonstrates that the imputation framework developed for corn is also effective for other crops such as rice and a dicot soy. The accuracy of the haplotype imputation for rice and soy were significantly high as demonstrated above.

Example 4

Imputing Molecular Phenotypes

Many molecular features of interest—such as gene expression, chromatin accessibility, DNA methylation, histone modifications, and transcription factor binding status, hereafter referred to collectively as molecular phenotypes in this Example, are locally, or cis, regulated by short DNA sequences. Therefore, observed molecular phenotypes corresponding to a given haplotype within a specified stage and/or tissue may be inferred to exist within other samples from the population containing the same haplotype. Moreover, different tissues and stages have varying degrees of similarity at the molecular level, allowing some sharing of information at the levels of both haplotype and tissue. Within breeding program A, the latent space transformations and the haplotype framework were combined to optimally impute chromatin accessibility to the haplotype level in corn.

An assay for transposase-accessible chromatin was run using sequencing (ATAC-seq) on 11 tissues in 11 diverse inbred corn lines, with 2 of the inbred lines having data on every tissues. Although the inbred lines were chosen to represent the diversity of breeding program A maize germplasm, there were many locations of haplotype sharing between individual lines. Moreover, one line did not have high-density marker available and instead had its haplotypes imputed using the methods described in Examples 1 and 2. The sampled tissues included both root and shoot derived organs at stages ranging from early seedling (V1) to post-flowering (R1).

Following alignment of read data and calling of read depth peaks within individual samples, a variational autoencoder framework was trained in order to form a latent representation of peak sharing among haplotypes and tissues. One percent of the genome, as partitioned in physical space among the maize reference genome, was chosen to serve as the training set for the latent space. The encoder received the peak signal for a given region in all tissue replicates of all samples except for a query haplotype i in a query tissue j. All sample replicates from tissue j with the haplotype i at the given region of the genome were set to missing. The encoder transformed the peak signal inputs into a real-valued latent vector, as in Examples 1-3, which represented the co-occurrence of peaks among haplotypes and tissues. A sampled latent representation was then passed to the decoder, which then transformed the latent representation to a reconstruction of peak signals in all haplotypes and tissues. Optimization of the objective function then minimized the reconstruction error, with regularization based on the KL-divergence of the latent space distributions and unit Gaussians.

Figure 18:
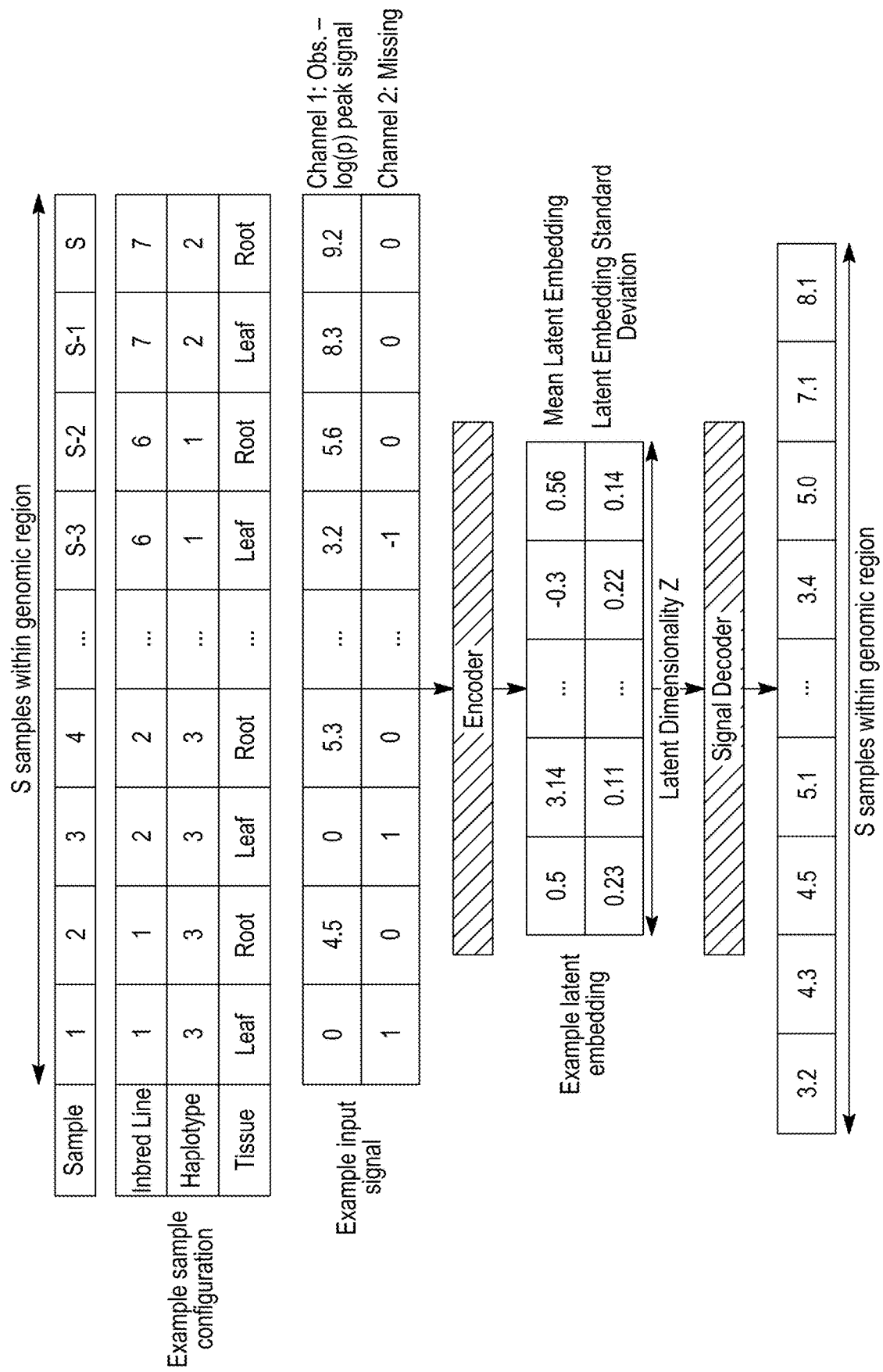

Example inputs and outputs for training an encoder for predicting molecular phenotypes are shown in FIG. 18. To do so, the haplotype for each inbred line within a genomic region is identified, and this information is combined with the known tissue type of each individual sample. For each sample, Channel 1 indicates a value obtained from $-\log(p)$ peak signal of an individual sample run with a peak-calling algorithm, and Channel 2 indicates whether a peak is designated as missing. For the purpose of training the neural network, one or more signals in a tissue and haplotype of interest is set to be missing. Specifically, in the illustrative embodiments, peaks for Haplotype 3 in leaf (i.e., Samples 1 and 3) are set to be missing, as indicated by value 0 in Channel 1 and value 1 in Channel 2. Subsequently, measurements of individual sample peak intensities are passed to an encoder with the missing peaks of Samples 1 and 3. The decoder is simultaneously trained to reconstruct the full set of signals. The output data may be used for further training.

Figure 19:
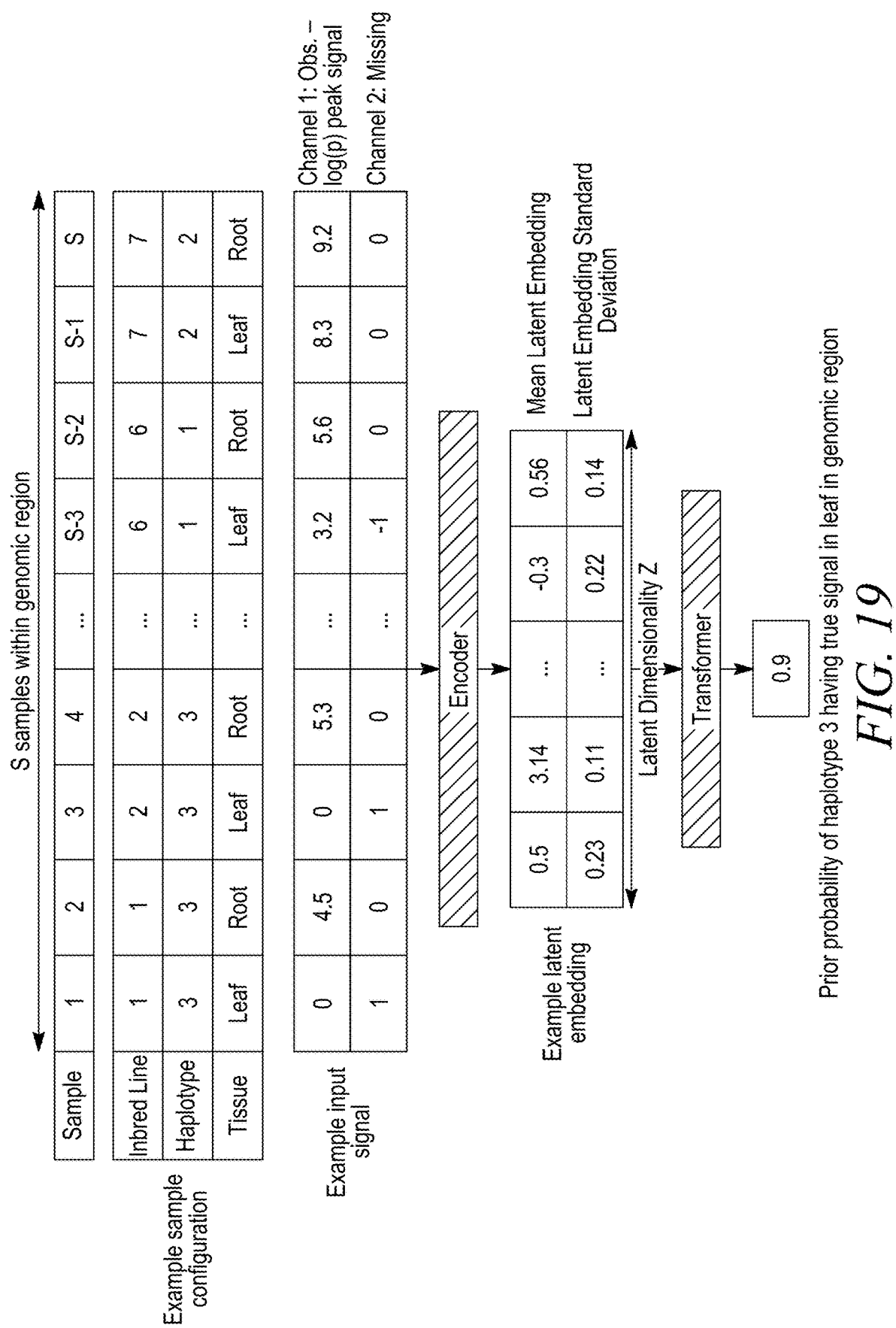

Additionally, example inputs and outputs for training a transformer for predicting molecular phenotypes are shown in FIG. 19. The parameters for the encoder are held constant, while the transformer is trained to predict the prior probability of true signal within a given haplotype and tissue combination, which is set to be missing within the input (i.e. Samples 1 and 3). In other words, even though signals of Haplotype 3 in leaf (i.e., Samples 1 and 3) were set to be missing, a prior probability of Haplotype 3 having true signal in leaf in genomic region is 0.9. This prior information can then be combined with the data from the missing input via a likelihood function in order to quantify the full evidence of true signal within the genomic region.

After fitting of the latent space, training of a transformer network began within the context of a probabilistic model of ATAC-seq signal. The transformer network received the latent representation as input and transformed it into the prior probability of a signal in a tissue and haplotype of interest. The input to the encoder remained the signals for all haplotypes and tissues except that of interest, allowing the prior probabilistic model to be informed by only information outside of the desired inference space. This prior model was then incorporated into a mixture model of two distributions, one denoting values emanating from true underlying chromatin accessibility signal and one denoting values from regions with zero true signal. Both were parameterized by gamma distributions, with terms for the power of specific replicates and—in the case of the true signal distribution—a term for the strength of the true signal. Inference was conducted using a Bayes factor that compared the marginal likelihoods of the observed signal strengths under the true signal and no signal distributions, with integration occurring over the true signal distribution. These Bayes factors factored in the prior probabilities for each distribution, thereby allowing haplotypes and tissues to share information.

The resulting model was evaluated using a combination of simulation and assessment of real data. Under simulation, with an empirically derived ratio of true versus no-signal regions and reasonable levels of sample noise, all true no-signal regions were found to have Bayes factors less than or equal to 1. Sensitivity was also reasonably high, with an area under the precision-recall curve greater than 0.8 for all tissues. Estimates of individual replicate statistical power and the covariance of signals among tissues were highly positively correlated with the true values. When applied to real data, approximately 5 million additional bases of peaks were able to be identified in the haplotypes corresponding to maize reference genome, beyond the peaks that could be identified without application of the haplotype framework. Sixty percent of this peak space was within 100 base pairs of a previously identified accessible region from a completely independent assay using micrococcal nuclease (MNase) sensitivity, which was 600% higher than the expectation under a random distribution relative to previously identified peaks.

This Example demonstrates that by employing the variational autoencoder-based training models, chromatin accessibility (a molecular phenotype) was predicted with greater accuracy than other methods.

Example 5

Predicting Agronomic Phenotypes

The latent representation of the genetic space also permits inference of genetic contributions to agronomic phenotypes, thereby enabling unified genomic prediction of crops even without shared marker sets. One phenotype of interest is the brittlesnap stalk lodging score provided by the screening of corn hybrids with a wind machine. Training and testing sets on measured brittlesnap scores were obtained, with the testing set stratified to contain hybrids such that 0, 1, or both of the parents were present within at least 1 training hybrid.

Figure 20:
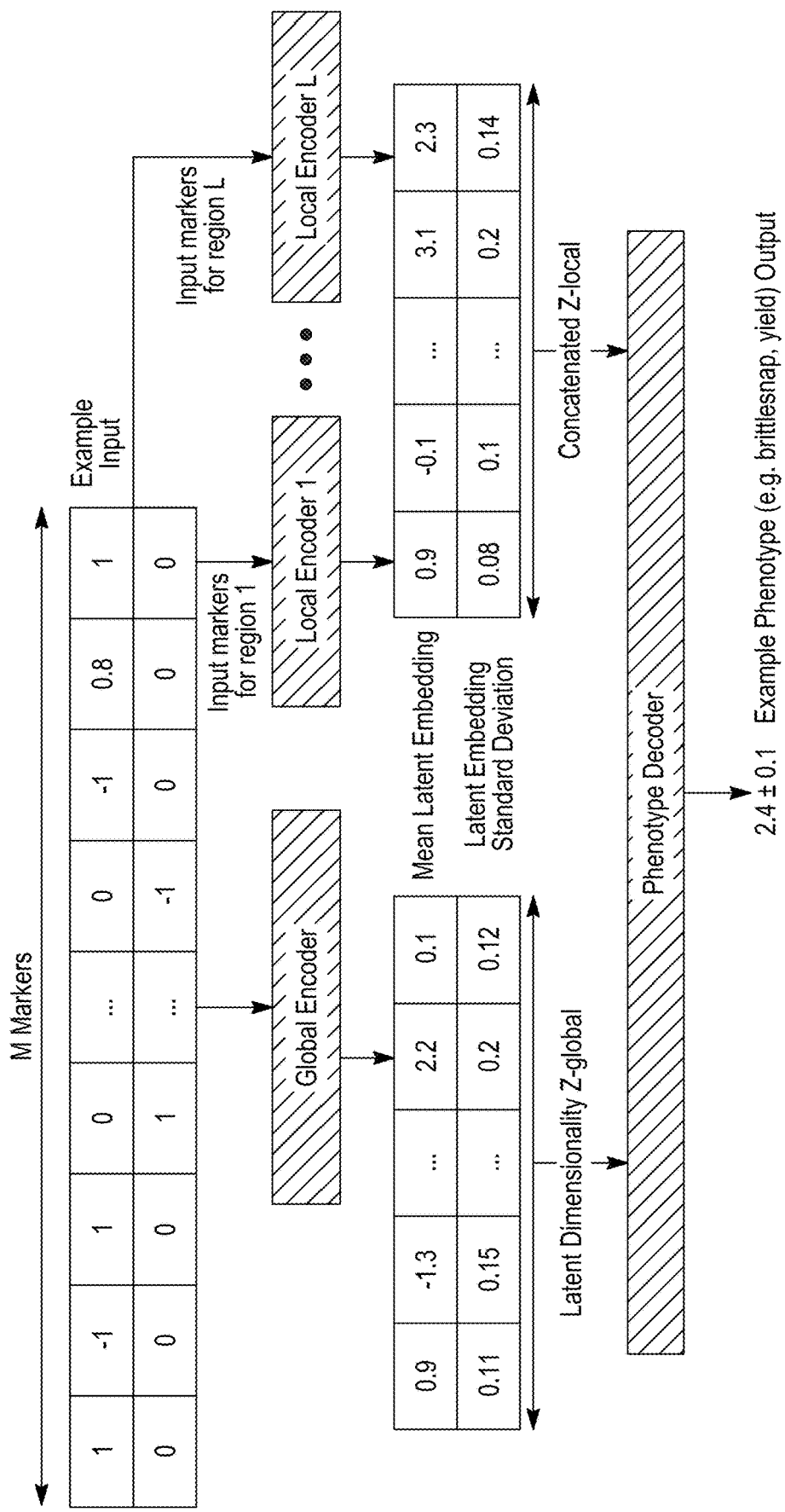

For example, as illustrated in FIG. 20, the global and local encoders were trained as outlined in Examples 1 and 2, and a decoder was trained to receive the global and local encoder representations of a given hybrid's parents as input. It should be appreciated that, in the illustrative embodiment, each local encoder is associated with each phenotype. Although only one phenotype decoder is shown in FIG. 20, it should be appreciated that there are different phenotype decoders for each phenotype. The decoder's output (2.4±0.1) consisted of a continuous prediction of the brittlesnap score. It should be appreciated that the weights of the global and local encoders were fixed during training, while those of the decoder were updated in order to minimize the prediction error for the phenotypic scores.

Following completion of training, testing accuracy was evaluated on the held-out hybrids. Accuracy was measured via the Pearson's correlation coefficient between the predicted and observed brittlesnap score. The accuracy for hybrids with 1 inbred completely absent from the training set was 0.625, while that for hybrids with both inbred parents somewhere in the training set—but not including the testing combination—was 0.737. These values were highly correlative of the phenotype. This Example demonstrates that a commercially relevant agronomic characteristic was predicted based upon the variational autoencoder framework described herein.

Example 6

Population Coancestry from Latent Space

The coancestry between any two samples is a fundamental metric for performing quantitative genetics analyses. Because the latent space transformation of the genetic space allows for a marker-invariant (or marker independent) representation of the underlying genetics, it can also be used for the calculation of population-genetics features such as the coancestry between samples, as shown in FIG. 7.

Following the training of the global encoder, a decoder was trained to calculate the coancestry between any two inbred lines in corn given the global latent representation of each line. Training proceeded with a combination of observed genotypes and in silico crosses between them, as outlined in Examples 1-3. All observed genotypes used during training were the same as the genotypes used for the training of the global encoder, with a separate test set held out for final assessment of accuracy. Random dropout of input markers to the global encoders was also performed, as outlined in Examples 1-3. The weights of the global encoder were not updated during training. The objective function was set to minimize the error between the predicted coancestry and the observed coancestry, as calculated by the fraction of haplotype bins between any two lines that were identical in state. Finally, sampling of the training pairs was stratified according to true coancestry, such that pairs with coancestry within bins of 0-0.1, 0.1-0.2, 0.2-0.3, 0.3-0.5, and 0.5-1 were sampled at even rates. This stratification scheme was motivated by the predominance of pairs with near-zero coancestry, which led to higher variance of high coancestry predictions in the absence of stratification.

Figure 17:
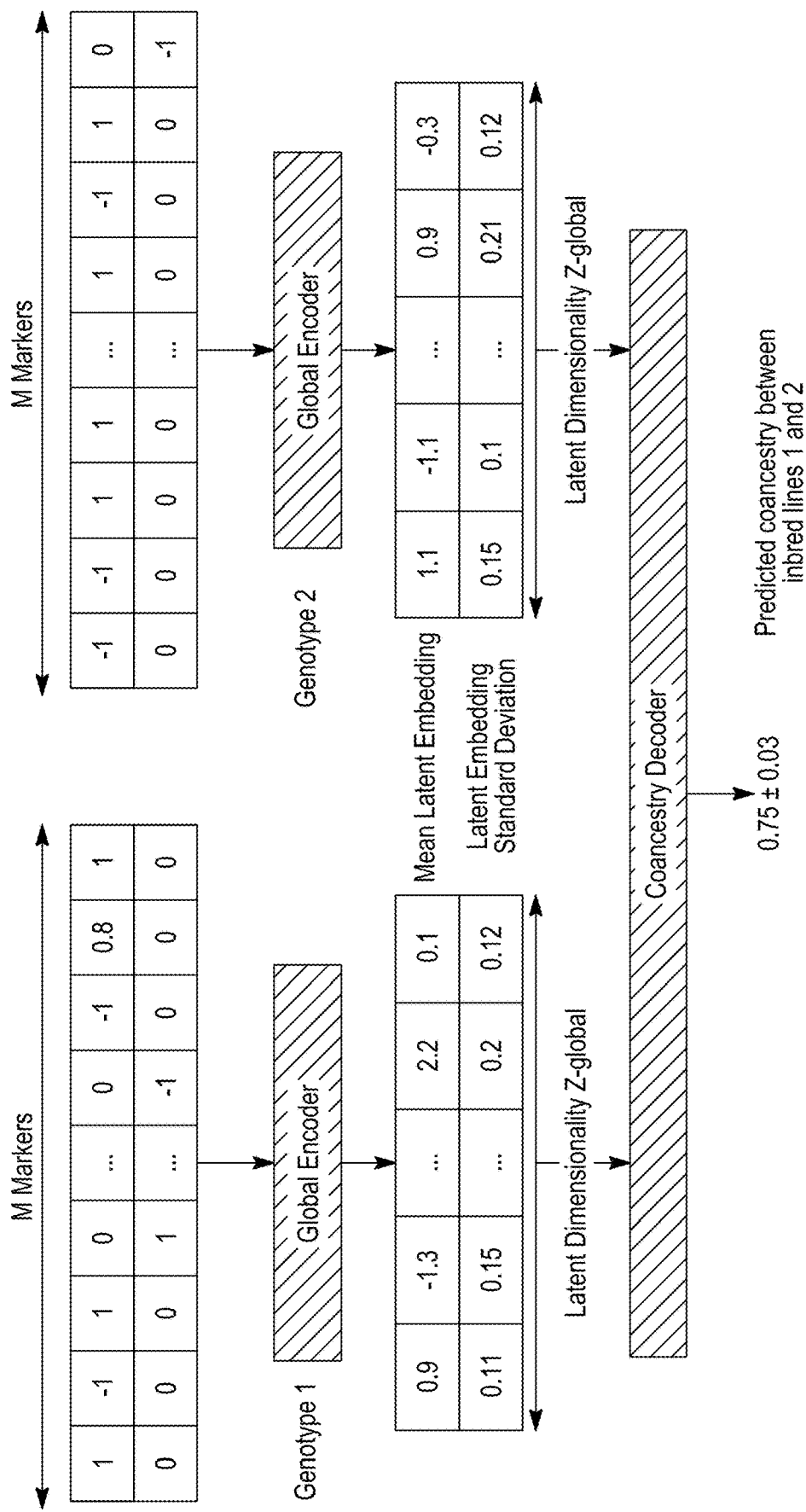

For example, training of a coancestry decoder from a latent space is described in FIG. 17. The coancestry decoder receives inputs from the global encodings of two different genotypes (i.e., inbred lines 1 and 2). It outputs an estimate of the coancestry between the genotypes as well as an estimate of the uncertainty in that prediction. In this example, the predicted value of the coancestries between inbred lines 1 and 2 was 0.75±0.03.

Following training, accuracy of the coancestry calculation was assessed on a random set of 3200 pairs if inbred lines within the testing set. The overall Pearson's correlation between the predicted and true coancestries was 0.964, with the mode of the predicted values following the diagonal and indicating good calibration of the predicted coancestries. Thus, this Example demonstrates that variational autoencoder framework can be used to determine ancestry relationships of two or more individual lines based on the latent representations of those lines. This latent representation can be marker-invariant or marker-independent, providing a powerful way to examine ancestry relationships without the need to do extensive marker analysis using the same marker set.

What is claimed:

1. A method of parametrically representing genotypic or phenotypic data obtained from one or more plant populations to impute or predict a genotype or phenotype of interest associated with an agronomic trait, the method comprising:
   providing genotypic or phenotypic data obtained from one or more plant populations;
   generating a universal latent space representation by encoding discrete or continuous variables derived from genotypic or phenotypic data into latent vectors through a machine learning-based encoder framework in a computer system, wherein the latent space representation is independent of the underlying genotypic or phenotypic data;
   decoding the latent space representation by a decoder, thereby imputing or predicting the genotype or phenotype of interest by the decoded latent representation; and
   selecting one or more plant populations or members thereof based on the imputed or predicted genotype or phenotype of interest, wherein the imputed or predicted genotype or phenotype of interest is associated with an agronomic trait.

2. The method of claim 1, wherein the genotypic data comprises a collection of genotypic markers or single nucleotide polymorphisms (SNPs).

3. The method of claim 2, wherein a subset of the genotypic markers or SNPs are from a plurality of genetically divergent plant populations.

4. The method of claim 1, wherein a subset of the discrete variables is a plurality of genotypic markers or SNPs localized to a chromosomal segment.

5. The method of claim 1, wherein the encoder framework is based on a neural network algorithm.

6. The method of claim 1, wherein the imputed or predicted genotype of interest is a plurality of haplotypes.

7. The method of claim 1, wherein the decoder imputes or predicts local high-density (HD) SNPs.

8. The method of claim 1, wherein the genotypic data is obtained from populations of plants derived from two or more breeding programs, wherein the breeding programs do not comprise an identical set of genotypic markers or SNPs corresponding to the genotypic data.

9. The method of claim 1, wherein the decoder imputes or predicts local high-density (HD) SNPs of one population based on the decoding of genotypic data of another population.

10. The method of claim 1, wherein the decoder imputes or predicts haplotypes for one population based on the decoding of genotypic data of another population.

11. The method of claim 1, wherein the decoder imputes or predicts population coancestry for one or more populations.

12. The method of claim 1, the method comprising: training the decoder to learn a prediction or imputation of a genotype or phenotype of interest based on an objective function for the encoded latent vectors.

13. The method of claim 12, the method further comprising: decoding by the decoder the encoded latent vector for the objective function.

14. The method of claim 13, the method comprising: providing an output for the objective function of the decoded latent vector.

15. The method of claim 1, the method comprising crossing with another population or member the one or more selected populations or members thereof imputed or predicted to comprise a genotype of interest, wherein the genotype of interest is associated with a desirable agronomic trait.

16. The method of claim 1, the method comprising counter-selecting from a breeding program the one or more selected populations or members thereof imputed or predicted to comprise a genotype of interest, wherein the genotype of interest is associated with an undesirable agronomic trait.

17. The method of claim 1, the method comprising crossing with another population or member the one or more selected populations or members thereof imputed or predicted to comprise a phenotype of interest, wherein the phenotype of interest is associated with a desirable agronomic trait.

18. The method of claim 1, the method comprising counter-selecting from a breeding program the one or more selected populations or members thereof imputed or predicted to comprise a phenotype of interest, wherein the phenotype of interest is associated with an undesirable agronomic trait.

19. The method of claim 1, wherein the plant is a soybean, maize, sorghum, cotton, canola, sunflower, rice, wheat, sugarcane, alfalfa tobacco, barley, cassava, peanuts, millet, oil palm, potatoes, rye, or sugar beet plant.

20. The method of claim 1, wherein the predicted phenotype of interest is yield gain.

21. The method of claim 1, wherein the imputed or predicted phenotype of interest is root lodging, stalk lodging, brittle snap, ear height, grain moisture, plant height, disease resistance, drought tolerance, or a combination thereof.

22. The method of claim 1, wherein the decoder imputes or predicts a molecular phenotype selected from gene expression, chromatin accessibility, DNA methylation, histone modifications, recombination hotspot, genomic landing locations for transgenes, transcription factor binding status, or a combination thereof.

23. A computing device comprising a processor configured to perform the steps of the method: providing genotypic or phenotypic data obtained from one or more plant populations; generating a universal latent space representation by encoding discrete or continuous variables derived from genotypic or phenotypic data into latent vectors through a machine learning-based encoder framework in a computer system, wherein the latent space representation is independent of the underlying genotypic or phenotypic data; decoding the latent space representation by a decoder, thereby imputing or predicting the genotype or phenotype of interest by the decoded latent representation; and selecting one or more plant populations or members thereof based on the imputed or predicted genotype or phenotype of interest, wherein the imputed or predicted genotype or phenotype of interest is associated with an agronomic trait.

24. A computer-readable medium comprising instructions which, when executed by a computing device, cause the computing device to carry out the steps of: providing genotypic or phenotypic data obtained from one or more plant populations; generating a universal latent space representation by encoding discrete or continuous variables derived from genotypic or phenotypic data into latent vectors through a machine learning-based encoder framework in a computer system, wherein the latent space representation is independent of the underlying genotypic or phenotypic data; decoding the latent space representation by a decoder, thereby imputing or predicting the genotype or phenotype of interest by the decoded latent representation; and selecting one or more plant populations or members thereof based on the imputed or predicted genotype or phenotype of interest, wherein the imputed or predicted genotype or phenotype of interest is associated with an agronomic trait.

25. A method of parametrically representing genotypic data obtained from one or more maize populations or sample set to impute or predict a genotype of interest associated with an agronomic trait, the method comprising:
generating a universal latent space representation by encoding discrete or continuous variables derived from genotypic data into latent vectors through a variational autoencoder, wherein the latent space representation is independent of the underlying genotypic data;
decoding the latent space representation by a decoder, thereby imputing or predicting the genotype of interest by the decoded latent representation; and
selecting one or more maize populations or members thereof based on the imputed or predicted genotype or phenotype of interest, wherein the imputed or predicted genotype or phenotype of interest is associated with an agronomic trait.

* * * * *